US007632636B2

(12) United States Patent
Roof et al.

(10) Patent No.: US 7,632,636 B2
(45) Date of Patent: Dec. 15, 2009

(54) PORCINE REPRODUCTIVE AND RESPIRATORY SYNDROME ISOLATES AND METHODS OF USE

(75) Inventors: Michael Roof, Ames, IA (US); Eric Vaughn, Ames, IA (US); Wesley Johnson, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 662 days.

(21) Appl. No.: 11/022,262

(22) Filed: Dec. 23, 2004

(65) Prior Publication Data

US 2006/0063148 A1 Mar. 23, 2006

Related U.S. Application Data

(60) Provisional application No. 60/611,824, filed on Sep. 21, 2004.

(51) Int. Cl.
*C12Q 1/70* (2006.01)
(52) U.S. Cl. .......................................................... 435/5
(58) Field of Classification Search ...................... 435/5, 435/237; 424/204.1, 186.1, 232.1, 218.1, 424/229.1
See application file for complete search history.

(56) References Cited

U.S. PATENT DOCUMENTS

2002/0172690 A1* 11/2002 Calvert et al. ............ 424/204.1

OTHER PUBLICATIONS

Labarque et al., "Effect of cellular changes and onset of humoral immunity on the replication of porcine reproductive and respiratory syndrome virus in the lungs of pigs," Journal of General Virology, 81:1327-1334 (2000).*
Halbur et al., "Effects of different US isolates of porcine and reproductive and respiratory syndrome virus on blood and bone marrow parameters of experimentally infected pigs," The Veterinary Record, p. 344-347 (2002).*
Shin et al., "Assessment of Porcine Reproductive and Respiratory Syndrome Virus RNA Load in Sera and Tissues during Acute Infection," J. Vet. Sci., 3(2), pp. 75-85 (2002).*
van der Linden et al (Vaccine 21:1952-1957, 2003).*
Quantitative relationship of systemic virus concentration on growth and immune response in pigs; L.L. Greiner, T.S. Stahly, and T.J. Stabel; Department of Animal Science Iowa State Univ Ames IA and National Animal Disease Center, Ames, IA; pp. 2690-2695, Journal of Animal Science 78:2690-2695, 2000.
A Simple Method of Estimating Fifty Per Cent Endpoints, The American Journal of Hygiene; L.J. Reed and H. Muench; vol. 27, May, 1938, No. 3; pp. 493-497.
Adjuvant Danger Signals Increase the Immune Response to Porcine Reproductive and Respiratory Syndrome Virus; Dennis L. Foss, Michael J. Zillox, William Meier, Federico Zuckermann, and Michael P. Murtaugh; Viral Immunology, vol. 15, No. 4, 2002 pp. 557-566.

Clinical effects of porcine reproductive and respiratory syndrome virus on pigs during the early postnatal invterval; William L. Mengeling, Kelly M. Lager, Ann C. Vorwald; AJVR, vol. 59, No. 1, Jan. 1988; pp. 52-55.
Clinical Manifestations of PRRS Virus: B. Thacker; 2003 PRRS Compendium, 2nd Edition; pp. 7-15.
Clinical signs and economic losses caused by porcine reproductive and respiratory syndrome virus in a large breeding farm; Zygmunt Pejsak, Tomasz Stadejek, Iwona Markowska-Daniel; Veterinary Microbiology.55,(1997) pp. 317-322.
Comparative pathogenicity of nine US porcine reproductive and respiratory syndrome virus (PRRSV) isolates in a five-week-old cesarean-derived, colostrum-deprived pig model; Patrick G. Halbur, Prem S. Paul, Xiang-Jin Meng, Melissa A. Lum, John J. Andrews, John A. Rathje; College of Veterinary Medicine, Iowa Statue Univ.; Ames, IA; pp. 11-20, J. Vet. Diagn. Invest. 8:11-20, 1996.
Comparative safety and efficacy of attenuated single-strain and multi-strain vaccines for porcine reproductive and respiratory syndrome; William L. Mengeling, Kelly M. Lager, Ann C. Vorwald, Deborah F. Clouser, Veterinary Microbiology 93 (2003) pp. 25-38.
Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR 2385, and Two Recent Field Isolates of PRRSV; T. Opriessnig, P.G. Halbur, K-J Yoon, R.M. Pogranichniy, K.M. Harmon, R. Evans, K.F. Key, F.J. Pallares, P. Thomas and X.J. Meng; Journal of Virology, Dec. 2002, pp. 11837-11844.
Complete genome comparison of porcine reproductive and respiratory syndrome virus parental and attenuated strains; Shishan Yuan, Daniel Mickelson, Michael P. Murtaugh, Kay S. Faaberg; Virus Research 74 (2001) pp. 99-110.
Effects of different US isolates of porcine reproductive and respiratory syndrome virus (PRRSV) on blood and bone marrow parameters of experimentally infected pigs; P.G. Halbur, F.J. Pallares, J.A. Rathje, R. Evans, W.A. Hagemosser, P.S. Paul, X.J. Meng: The Veterinary Record, Sep. 21, 2002, pp. 344-348.
Effects of Low (Modified-live Virus Vaccine) and High (VR-2385)-Virulence Strains of Porcine Reproductive and Respiratory Syndrome Virus on Pulmonary Clearance of Copper Particles in Pigs; R. Thanawongnuwech, P.G. Halbur, M.R. Ackermann, E.L. Thacker, and R.L. Royer; Veterinary Pathology, Iowa State University, Ames, IA (1998) ; pp. 398-406, Vet. Pathol. 35:398-406, 1998.

(Continued)

*Primary Examiner*—Mary E Mosher
(74) *Attorney, Agent, or Firm*—Michael P. Morris; Mary-Ellen M. Devlin; Joyce L. Morrison

(57) ABSTRACT

A method of predicting the virulence of a new or uncharacterized PRRS virus strain is provided wherein the strain is injected into swine and allowed to replicate for a period of from about 3-15 days. During this period, the rate of virus growth and/or the magnitude of viremia is determined, and this data is compared with a corresponding growth rate and/or viremia magnitude of a PRRS virus strain of known virulence, as a measure of the virulence of the new or uncharacterized strain.

11 Claims, 9 Drawing Sheets

OTHER PUBLICATIONS

Efficacy of modified live virus porcine reproductive and respiratory virus vaccines against heterologous respiratory challenge; M.B. Roof, E.M. Vaughn, K.M. Burkhart, K.S. Faaberg; Boehringer Ingelheim Vetmedica Inc. Research and Development, Ames, IA, USA, Dept of Veterinary Pathobiology, University of Minnesota, St. Paul, MN; 4th International Symposium on Emerging and Re-emerging Pig Diseases-Rome, Jun. 29-Jul. 2, 2003, pp. 117-118.

Evolution of Porcine Reproductive and Respiratory Syndrome Virus during Sequential Passages in Pigs; C.C. Chang, K.J. Yoon, J.J. Zimmerman, K.M. Harmon, P.M. Dixon, C.M.T. Dvorak and M.P. Murtaugh; Journal of Virology, May 2002, pp. 4750-4763.

Genetic variation and phylogenetic analyses of the ORF5 gene of acute porcine reproductive and respiratory syndrome virus isolates: Kijona F. Key, Gholamreza Hasqshenas, Denis K. Guenette, Sabrina L. Swenson, Thomas E. Toth, Xiang-Jin Meng; Veterinary Microbiology 83 (2001) pp. 249-263.

Genetic variation and phylogenetic relationships of 22 porcine reproductive and respiratory syndrome virus (PRRSV) field strains based on sequence analysis of open reading frame 5; V.G. Andreyev, R.D. Wesley, W.L. Mengeling, A.C. Vorwald and K.M. Lager; Archives of Virology (1997) 142; pp. 993-1001.

Genetic variation in porcine reproductive and respiratory syndrome virus isolates in the midwestern United States; V. Kapur, M.R. Elam, T.M. Pawlovich and M.P. Murtaugh; Journal of General Virology (1996) 77, pp. 1271-1276.

Genetic variation in the PRRS Virus; M.P. Murtaugh, K.S. Faaberg, J. Laber, M. Elam and V. Kapur; Dept. of Veterinary PathoBiology, University of Minnesota, St. Paul, MN; pp. 787-794, 1998.

Genomic characterization of virulent, attenuated, and revertant passages of a North American porcine reproductive and respiratory syndrome virus strain; T.V. Grebennikova, D.F. Clouser, A.C. Vorwald, M.I. Musienko, W.L. Mengeling, K.M. Lager, R.D. Wesley, S.F. Biketov, A.D. Zaberezhny, T.I. Aliper and E.A. Nepokionov; Virology 321 (2004) pp. 383-390.

Heterogeneity of porcine reproductive and respiratory syndrome virus; implications for current vaccine efficacy and future vaccine development; X.J. Meng; Veterinary Microbiology 74 (2000) pp. 309-329.

Identification of Neutalizing and Nonneutralizing Epitopes in the Porcine Reproductive and Respiratory Syndrome Virus GP5 Ectodomain; M. Ostrowskl, J.A. Galeota, A.M. Jar, K.P. Platt, F.A. Osorio, and O.J. Lopez; Journal of Virology, May 2002, pp. 4241-4260.

Immune responses in pigs infected with porcine reproductive and respiratory syndrome virus (PRRSV); E. Albina, L. Piriou, E. Hutet, R. Cariolet, R.L. Hospitalier, Veterminary Immunology and Immunopathology 61 (1998) pp. 49-66.

Immunological Responses of Swine to Porcine Reproductive and Respiratory Syndrome Virus Infection; Michael P. Murtaugh, Zhengguo Xiao, and Federico Zuckerrnann; Viral Immunology, vol. 15, No. 4, 2002; pp. 533-547.

Is Human Immunodeficiency Virus RNA Load Composed of Neutralized Immune Complexes?: Ferdinando Diazani, Guido Antonelli, Elisabetta Riva, Ombretta Turriziani, Laura Antonelli, Stephen Tyring, Daniel A. Carrasco, Hung Lee, Derrick Nguyen, Jingzhi Pan, Joyce Poast, Miles Cloyd, and Samuel Baron; Journal of Infectious Diseases 2002:185; pp. 1051-1054.

Role of Viral Porteases in PRRS Immunity; Final Report: Aug. 30, 2003; Michael P. Murtaugh; Dept. of Veterinary PathoBiology, University of Minnesota, St. Paul, MN and Boehringer Ingelheim Vetmedica Inc, Ames IA: pp. 1-38, 2003.

Nidovirales: a new order comprising Coronaviridae and Arterviridae; D. Cavanagh; Virology Divison News; Arch Virol 142/3 (1997); pp. 629-633.

Overview and History of Mystery Swine Disease (Swine Infertility/Respiratory Syndrome); Howard Hill, D.V.M., Ph.D., Veterinary Diagnostic Laboratory, Iowa State University: Mystery Swine Disease Committee Meeting; Livestock Conservation Institute—Proceedings; pp. 29-40, Proceedings, Mystery Swine Disease Committee Meeting, 1990.

Respiratory tract protection upon challenge of pigs vaccinated with attenuated porcine reproductive and respiratory syndrome virus vaccines; G. Labarque, S. Van Gucht, K. Van Reeth, H. Nauwynck, M. Pensaert; Veterinary Microbiology 95 (2003); pp. 187-197.

Strain specificity of the Immune response of pigs following vaccination with various strains of porcine reproductive and respiratory syndrome virus; William L. Mengeling, Kelly M. Lager, Ann C. Vorwald, Kenneth J. Koehler; Veterinary Microbiology 93 (2003); pp. 13-24.

Temporal and Morphotogic Characterization of the Distribution of Porcine Reproductive and Respiratory Syndrome Virus (PRRSV) by in Situ Hybridization in Pigs Infected with Isolates of PRRSV that Differ in Virulence; J.S. Haynes, P.S. Halbur, T. Sirinarumitr, P.S. Paul, X.J. Meng, and E.L. Huffman; Veterinary Pathology 34 (1997) 39-43.

Erratum to "Complete genome comparison of porcine reproductive and respiratory syndrome virus parental and attenuated strains" [Virus Research 74 (2001) 99-110]; Shishan Yuan, Daniel Mickelson, Michael P. Murtaugh, Kay S. Faaberg; Virus Research 79 (2001) p. 187.

* cited by examiner

PORCINE REPRODUCTIVE AND RESPIRATORY SYNDROME ISOLATES AND METHODS OF USE

This application is a nonprovisional and claims the priority benefit of application Ser. No. 60/611,824 filed Sep. 21, 2004.

BACKGROUND OF THE INVENTION

1. Field of the Invention

The present invention is concerned with new isolated wild-type PRRS virus strains and corresponding improved attenuated PRRS viruses, as well as methods of measuring the magnitude of viremia, rate of growth, antibody response, and combinations thereof in such strains and viruses. More particularly, the present invention provides methods for predicting the virulence of new or previously uncharacterized PRRS strains.

2. Description of the Prior Art

Porcine reproductive and respiratory syndrome virus (PRRSV) is an enveloped single stranded RNA virus classified in the family Arteriviridae (Cavanaugh, 1997). It causes a widespread disease of swine that was first described as 'mystery swine disease' in the USA in 1987 (Hill, 1990). The disease manifests as respiratory illness in all age groups of swine leading to death in some younger pigs and severe reproductive problems in breeding age females.

The dynamic nature of PRRSV allows for constant change in the disease and provides ample opportunity for the appearance of new strains (Andreyev et al., 1997; Murtaugh et al. 1998; Meng, 2000). The fact that PRRSV changes so readily, coupled with its ability to cause devastating problems for swine producers, makes it an important subject for research (Mengeling et al., 1998; Pejsak et al., 1997) and for the development of vaccines and other methods of reducing the effects of infection. Variation in levels of isolate virulence were demonstrated in lung lesions, and death in swine (Halbur et al., 1996), but efforts to link biological and immunological differences to specific genetic differences has been largely unsuccessful (Albina et al., 1998; Key et al., 2001; Yuan et al., 2001; Murtaugh et al., 2002; Grebennikova et al., 2004). Studies examining the safety and efficacy of PRRS vaccines include the work of Labarque et al., (2003), Mengeling et al., (2003a), and Nodelijik et al. (2001). These studies show that under experimental conditions, modified live PRRS vaccines reduce the amount and duration of viremia as well as fever and lung lesions after virulent challenge.

Opriessing et al. (2002) showed that isolates with high amino acid sequence homology in open reading frame 5 (ORF5) caused significantly different levels of pneumonia in pigs. Variation in swine responses to PRRSV also are affected by host variation (Mengeling et al., 2003b). Virulence has been examined in relation to replication rates and distribution of PRRSV in pigs (Haynes et al., 1997), to macrophage copper clearing capabilities (Thanawongnuwech et al., 1998), and the anemia levels of the host animal (Halbur et al, 2002). However, these methods have been deficient in providing effective methods for predicting the virulence of new or previously uncharacterized PRRS strains.

Accordingly, what is needed in the art is a method of predicting the virulence of PRRS strains. What is further needed in the art is a method of predicting the virulence of PRRS strains based on the rate of in vivo PRRS viral growth and/or viremia magnitude in a swine after administration or exposure of the strain to a previously PRRS-free swine.

SUMMARY OF THE INVENTION

The present invention overcomes the problems outlined above and provides methods for predicting the degree of virulence of a new or uncharacterized PRRS virus strain. The methods generally involve assessing a new or previously uncharacterized strain of PRRS for at least one of the following parameters: rate of viral growth; magnitude of viremia; antibody response; or combinations thereof. The results of such an assessment are then used to predict the degree of virulence of the new or previously uncharacterized strain. The methods generally involve administering or exposing a PRRS-free swine to a quantity of the new or uncharacterized PRRS strain and allowing the virus to replicate for a period of up to about 15 days, more preferably from about 2-12 days, still more preferably from about 3-10 days and still more preferably from about 3-7 days. The mode of administration can be accomplished using any conventional manner, including oral, intranasal, intramuscular, intra-lymph node, intradermal, intraperitoneal, subcutaneous, and combinations thereof, but most preferably through intranasal administration. The amount of the dose for intranasal administration is preferably up to about 5 ml, still more preferably between about 0.5 ml to about 4 ml, still more preferably between about 1 ml and about 3 ml, and still more preferably about 2 ml. The concentration of virus in each dose should be up to about $5.0 \log_{10} TCID_{50}$/ml, more preferably between about 1.0 to about $4.0 \log_{10} TCID_{50}$/ml, and still more preferably about 2.5 to $3.5 \log_{10} TCID_{50}$/ml, and most preferably about $3.0 \log_{10} TCID_{50}$/ml. At a selected time or times during this replication period, biological samples are taken from the swine and measurements of the rate of growth of the administered virus, viremia magnitude, antibody response, and/or combinations thereof are taken. Data gathered from these measurements is then compared with the rate of growth, viremia magnitude, antibody and/or combinations thereof for a known and characterized strain, as a measure of predicted virulence of the new or unknown strain.

Using the methods of the present invention, the rate of PRRS viral growth, viremia magnitude, antibody response, and/or combinations of these characteristics were measured in swine which had one of eight different PRRSV isolate strains administered thereto. Each of these strains had a known level of virulence and clinical disease manifestations. These same characteristics were also measured in swine which had a combination of all eight strains administered thereto.

More specifically, one hundred (100) healthy two-three week old pigs were divided randomly by weight into ten groups with each group having ten pigs. All pigs were tested for PRRS infection using HerdChek® PRRS ELISA 2XR (IDEXX Laboratories Inc., Westbrook, Me.). Eight of the groups received an administration of one of the eight strains, one group received an administration consisting of a combination of all eight strains, and the last group received an administration Eagle's Minimum Essential Medium (EMEM) to act as a control group. A sample of each viral inoculation was retitrated for titer confirmation. Preferably the titer of the administered virus is designed to mimic a natural exposure level of virus. Biological samples in the form of blood were collected at various times throughout the 49-day experiment. Each sample was analyzed by virus isolation, quantitative reverse transcriptase-polymerase chain reaction (RT-PCR), HerdChek® PRRS ELISA 2XR, and PRRSV protein-specific ELISA.

Virus isolation was performed on CL2621 cells by serially diluting serum and combining it with EMEM, gentamicin (Sigma Chemical Co., St. Louis, Mo.) and Fungizone (Invitrogen Corp., Grand Island, N.Y.). The dilutions were then incubated and examined for cytopathic effect (CPE). The Reed-Muench calculation was used to determine titers.

RT-PCR was performed using the QIAamp Viral RNA Mini-Kit® (Qiagen, Inc., Valencia, Calif.) and PRRSV was detected using a single-tube assay by Tetracore, Inc. (Gaithersburg, Md.). To determine virus quantitation, a standard curve was developed and concentrations of the unknown samples were determined by linear extrapolation of the cycle threshold values plotted against the known concentration of the 3' UTR transcript product.

Antibody measurement using ELISA S/P ratios were generated using HerdChek® PRRS ELISA 2XR using the manufacturer's instructions. PRRSV protein-specific ELISA was performed using recombinant isolate VR2332 nucleocapsid (N) and non-structural protein 4 (nsp 4) expressed in BL21 (DE3)-RP cells (Stratagene, La Jolla, Calif.).

All pigs were weighed at the beginning and at the end of the study. Additionally, on every day of the study, each pig was evaluated and scored by a veterinarian for clinical signs of PRRS disease. All resulting data was analyzed statistically and compared on a group-by-group basis.

As used herein, "rate of growth" refers to the measurement of virus replication over time in swine. Preferred examples of this measurement are provided in Example 1. "Viremia magnitudes" as used herein, refers to the concentration of virus circulating in the blood of swine. Preferred examples of this measurement are also provided in Example 1.

DETAILED DESCRIPTION OF THE PREFERRED EMBODIMENTS

Figure 1:
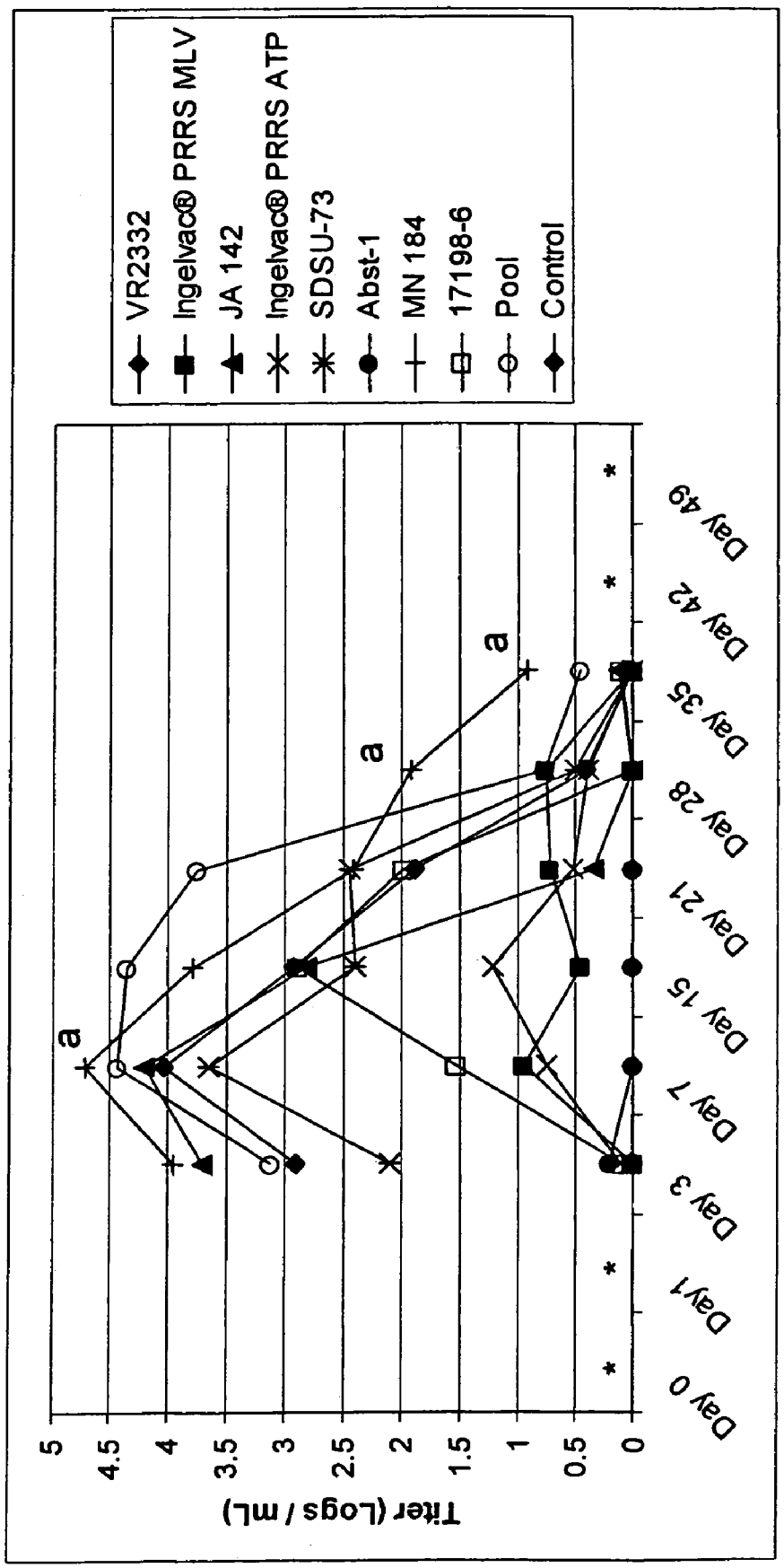
FIG. 1 is a graph of mean serum virus titer versus time expressed as $Log_{10}$ $TCID_{50}$/ml for the swine test of Example 1.

The following examples set forth preferred isolates and procedures in accordance with the present invention. It is to be understood, however, that these examples are provided by way of illustration only, and nothing therein should be deemed a limitation upon the overall scope of the invention.

EXAMPLE 1

Materials and Methods

One hundred healthy 2-3 week-old pigs were obtained from a PRRS-free commercial herd and were maintained at Veterinary Resources, Inc., Ames, Iowa, under the supervision of a veterinarian. Animals received food and water ad libitum. All of the animal care and laboratory personnel involved with the study were blinded to the treatments given to the various groups of animals. Pigs were tested by HerdChek® PRRS ELISA 2XR (IDEXX Laboratories Inc. Westbrook, Me.) to determine if any pigs were infected with PRRSV. All of the pigs for this example tested negative. The pigs were then randomly divided by weight into 10 groups with 10 pigs per group.

A total of eight PRRSV isolates were used in this example. These isolates have been designated VR-2332, Ingelvac® PRRS MLV, JA 142, Ingelvac® PRRS ATP, SDSU 73, Abst-1, MN 184, and 17198-6. These eight isolates span the history of PRRS disease, exhibit a wide range of virulence levels, and represent relevant clinical disease manifestations. All of the virus isolates grew readily on CL2621 cells (CL2621 is a proprietary cell line obtained from NVSL, Ames, Iowa, ) (an MA-104 monkey kidney cell line). Three of the primary field isolates, VR-2332, JA-142, and SDSU 73, also had attenuated forms, Ingelvac® PRRS MLV (Boebringer Ingelheim Vetmedica Inc., St. Joseph, Mo.), Ingelvac® PRRS ATP (Boebringer Ingelheim Vetmedica Inc., St. Joseph, Mo.), and Abst-1, respectively. These attenuated forms all exhibit low or undetectable virulence that was derived by in vitro passaging to attenuation. The PRRSV isolate ATCC VR-2332 was isolated in 1991 in Minnesota and was used at cell culture passage three. The attenuated form of this virus is commercially available under the trade-name Ingelvac® PRRS MLV. The PRRSV isolate JA 142, provided by William Mengeling, National Animal Disease Center, Ames, Iowa, was isolated in 1997 in Iowa from a severe "abortion-storm" case of reproductive failure and was used at cell culture passage five. The attenuated form of JA 142 is commercially sold under the trade-name Ingelvac® PRRS ATP and has been assigned ATCC No. VR-2638. PRRSV SDSU 73 (ATCC No. PTA-6322) was recovered in Iowa from a severe case of reproductive disease in 1996 and was used at cell culture passage one. The attenuated form of SDSU 73, designated Abst-1 (ATCC No. PTA-6320), was obtained by 52 passages. The PRRSV isolate 17198-6 (ATCC No- PTA-6321) was obtained from Oklahoma in 1997 from a herd experiencing severe reproductive disease and was used at passage level four. The PRRSV MN 184 isolate (ATCC No. PTA-6319) was obtained in 2001 from a swine farm experiencing severe reproductive disease and sow mortality in southern Minnesota and was provided by Kurt Rossow, University of Minnesota, St. Paul. This isolate was used at a cell culture passage of one. Additionally, a pool consisting of a combination of all isolates was produced.

On day 0, each of the eight PRRSV isolates and the PRRSV pool were diluted to approximately 3.0 $Log_{10}$ $TCID_{50}$/ml in Eagle's Minimum Essential Medium (EMEM) (JRH Bioscience, Lenexa, Kans.) containing 4% FBS (JRH Bioscience, Lenexa, Kans.) and administered intranasally to pigs at a dose of 2 ml (1 ml per nostril). The untreated control group received 2 ml of media. The inocula were retitrated on 96-well plates containing three-day-old CL2621 cells for titer confirmation using the Reed-Muench method (Reed et al., 1938). The observed titers administered to pigs, together with a description of the virulence level and isolation information, are shown in Table 1.

TABLE 1

Virulence and Inoculation Titer of Isolates.

| Group | Isolate | Year Isolated | Virulence*** | Titer $\log_{10}$ $TCID_{50}/ml$ |
|---|---|---|---|---|
| 1 | VR 2332 | 1991 | Moderate | 3.43 |
| 2 | Ingelvac® PRRS MLV* | USDA license 1996 | Attenuated VR2332 | 3.02 |
| 3 | JA 142 | 1997 | High | 3.13 |
| 4 | Ingelvac® PRRS ATP* | USDA license 1999 | Attenuated JA 142 | 4.14 |
| 5 | SDSU 73 | 1996 | High | 2.75 |
| 6 | Abst-1* | Attenuated 1999 | Attenuated SDSU 73 | 4.18 |
| 7 | MN 184 | 2001 | High | 4.10 |
| 8 | 17198-6 | 1997 | High | 2.81 |
| 9 | Pool** | N/A | High | 3.71 |
| 10 | Control | N/A | N/A | N/A |

*attenuated PRRSV isolates.
**Mixture containing all of the eight isolates
***Summary of lung lesions reported in Symposium on Emerging Diseases, Rome 2003.

The isolates were then compared to determine their genetic similarity through an analysis of their percent sequence identity. Sequence identity was determined by submitting virus samples to the University of Minnesota Diagnostic Laboratory for sequence analysis. The results of ORF 5-6 were provided and then compared to a PRRS virus consensus sequence. Individual base pair differences were noted and then the % sequence identity was compared between isolates. As those of skill in the art are aware, blast searching can also be done at various websites. For example, the University of Minnesota provides a PRRSV database (ccgb.umn.edu/cgi-bin/common/web_blast.cgi) that lists sequences from isolates from 1989-2003. Another frequently used site is the NCBI BLAST link found at ncbi.nlm.nih.gov/BLAST.

As shown by the percent sequence identity and the dendogram in Table 2, the virulent field isolates are quite genetically distinct and represented a diverse group of PRRSV isolates. In contrast, the parental and vaccine PRRSV pairs were nearly genetically identical. The pairwise comparison and dendrogram of Table 2 were generated using the Lasergene software suite of sequence analysis tools (DNASTAR, Inc, (Madison, Wis.)).

Evaluation of Viremia

Blood samples were collected from each pig in each group by vacutainer on days 0, 1, 3, 7, 15, 21, 28, 35, 42, and 49. Serum was separated from clotted whole blood by centrifugation at 3200×g for 20 minutes. Serum samples were then divided for analysis by virus isolation, $\text{Log}_{10}$ $TCID_{50}/ml$, quantitative reverse transcriptase-polymerase chain reaction (RT-PCR), HerdChek® PRRS ELISA 2XR, and PRRSV protein-specific ELISA. The serum samples in this study were processed immediately after collection and were chilled on ice within 3 hours of being obtained. The samples were stored for a maximum of 24 hr at 4° C. and at −70° C. thereafter. Serum tested by RT-PCR was frozen at −70° C. the day of collection and stored until the testing could be performed at which time only the number of samples that could be tested within 24 hours were thawed, extracted, and tested.

Virus isolation was performed on three-day-old CL2621 cells for samples collected on days 0, 1, 42, and 49. One hundred µl of serum from each pig on the remaining days of the study was diluted serially by ten-fold dilutions to a final dilution of $10^{-6}$ in tubes containing 900 µl of EMEM, 2% FBS, 50 µg/ml gentamicin (Sigma Chemical Co. St. Louis, Mo.), and 2.5 µg/ml Fungizone (Invitrogen Corporation, Grand Island N.Y.). Four replicates of each dilution were incubated on 96-well plates containing CL2621 cells, at 37° C. and 4.5% $CO_2$ for eight days. Each well then was examined for cytopathic effect (CPE) and the titers were determined using the Reed-Muench calculation.

To obtain viral RNA for quantitative RT-PCR the QIAamp Viral RNA Mini-Kit® (Qiagen Inc. Valencia, Calif.) was used as described in the kit instructions. A commercially available real-time, single-tube, RT-PCR assay for the detection of U.S. PRRSV was provided by Tetracore Inc. (Gaithersburg, Md.) and used to detect PRRSV RNA. A minor groove binding (MGB) 5' nuclease probe and primers were designed by alignment of GenBank isolates and based on conserved areas of the 3' untranslated region (UTR). PRRSV RNA was reverse transcribed in a 25 µl single tube reaction consisting of Tetracore U.S. PRRSV Master Mix (18.9 µl Master mix, 2 µl Enzyme mix 1, 0.1 µl Enzyme mix 2) and 4 µl of extracted RNA. The reaction tubes were loaded into the Smart Cycler II® block (Cepheid, Sunnyvale, Calif.) and software settings of fluorescent detection were set for automatic calculation of the baseline with the background subtraction on. The thermal

TABLE 2

Pairwise comparisons of ORF5 nucleotide sequence of virulent and attenuated PRRSV isolates used in the study. Percent similarity is shown in the upper right and percent divergence is shown in the lower left of the table. The dendrogram shows the genetic relatedness of the isolates. The bar indicates 1 nucleotide change per 100 residues. VR2332 is the parent isolate of Ingelvac PRRS MLV, JA 142 is the parent strain of Ingelvac PRRS ATP and SDSU 73 is the parent strain of Abst-1.

Percent Identity

|  | VR 2332 | Ingelvac PRRS MLV | JA-142 | Ingelvac PRRS ATP | SDSU 73 | Abst-1 | MN 184 | 17198-6 |
|---|---|---|---|---|---|---|---|---|
| VR 2332 |  | 99.7 | 91.0 | 90.5 | 90.0 | 89.6 | 86.4 | 90.4 |
| Ingelvac PRRS MLV | 0.3 |  | 90.7 | 90.2 | 89.7 | 89.2 | 86.4 | 90.0 |
| JA-142 | 9.7 | 10.1 |  | 99.2 | 92.7 | 92.2 | 87.2 | 92.2 |
| Ingelvac PRRS ATP | 10.3 | 10.7 | 0.8 |  | 91.9 | 91.4 | 86.4 | 91.4 |
| SDSU 73 | 10.9 | 11.3 | 7.8 | 8.8 |  | 99.5 | 87.2 | 91.7 |
| Abst-1 | 11.5 | 11.9 | 8.4 | 9.4 | 0.5 |  | 86.7 | 91.2 |
| MN 184 | 15.5 | 15.5 | 14.4 | 15.5 | 14.4 | 15.1 |  | 86.1 |
| 17198-6 | 10.5 | 10.9 | 8.8 | 9.7 | 9.0 | 9.6 | 15.9 |  |

Percent Divergence cycler program consisted of 52° C. for 1800 seconds, 95° C. for 900 seconds, and 45 cycles at 94° C. for 30 seconds, 61° C. for 60 seconds and 72° C. for 60 seconds. A PCR reaction was considered positive if the cycle threshold (Ct) level was obtained at ≦45 cycles. For quantitation, known amounts of serially diluted in vitro transcript RNA product ($1 \times 10^{-1}$ through $1 \times 10^8$ copies/µl) were used to generate a standard curve. Copy/ml concentrations of the unknown samples were determined by linear extrapolation of the Ct values plotted against the known concentration of the 3'UTR transcript product.

Antibody Measurement

ELISA S/P ratios were generated by performing the Herd-Chek® PRRS ELISA 2XR according to the manufacturer's instructions. PRRSV protein-specific ELISA for The Herd-Chek® was performed with recombinant isolate VR2332 nucleocapsid (N) and nonstructural protein 4 (nsp 4) which were expressed in BL21 (DE3)-RP cells (Stratagene) from the plasmid pET 24b as fusion proteins containing an amino terminal myc-tag and a carboxyl terminal 6× histidine tag. Denatured proteins were dialyzed in 0.1 M Tris HCl, pH 8.0, 6 M guanidine-HCl, 2 mM EDTA and adjusted to a concentration of 3 mg/ml. DTT was added to 300 mM and the solution was filtered through a 0.45 µm membrane. Reduced protein was added into refolding buffer (100 mM Tris HCl, pH 8.0, 0.5 M L-arginine, 8 mM oxidized glutathione, 2 mM EDTA, 10 µM pepstatin A, 10 µM leupeptin, and 1 mM PMSF), filtered (0.22 µm) and stirred overnight. The purified protein was concentrated by tangential flow filtration (Pellicon XL Ultracel PLC 5 kd, Millipore) and dialyzed against 20 mM Tris HCl, pH 8.0. Proteins were analyzed on an Agilent 2100 Bioanalyzer with the Protein LabChip. Purified protein solutions were stored at −80° C.

Protein-specific ELISAs were performed by coating microtiter plates with 100 ng recombinant protein in carbonate buffer, pH 9.6, or with buffer alone. Plates were blocked with 2.5% nonfat dry milk in phosphate-buffered saline containing 0.1% Tween 20 (PBST). One hundred µl of a 1:2000 dilution of serum was applied to duplicate wells for 2 hours, after which plates were washed with PBST and antibody binding was detected by incubation with horseradish peroxidase-conjugated goat-anti swine IgG (heavy+light chains (KPL, Gaithersburg Md.) diluted 1:5000 for 1 hour, followed by washing and color development with 100 µl of TMB substrate (KPL). Reactions were stopped with 1 M phosphoric acid and plates were read at 450 nm.

Body Weights

All pigs were weighed on day 0 (first day of study) and day 49 (end of study). Pigs were weighed on a portable electronic weigh-bar scale system Weigh-Tronix™ model 615XL, (Weigh-Tronix Inc., Fairmont, Minn.). The scale was calibrated using certified test weights prior to and after each use.

Clinical Scores

On every day of the study each pig was scored by a veterinarian for respiratory signs, behavior, and coughing on a scale of one to four for each clinical sign. A normal animal was given a score of three, maximum clinical illness was a score nine and a dead animal received a score of 12. Samples from all animals that died in the study were submitted to the Iowa State University Veterinary Diagnostic Laboratory for pathological examination.

Statistical Analysis

All data were imported into SAS version 8.02 for data management and analysis. Summary statistics including mean, standard deviation standard error, median and frequency distributions were generated for all out come variables as appropriate. Weight, RT-PCR, and $\text{Log}_{10} \text{TCID}_{50}/\text{ml}$ data were analyzed by one way ANOVA for overall differences among the treatment groups with pairwise testing for differences between treatment groups by Least Significant Difference t test. All tests for differences between groups were designed as two-sided tests. Differences were considered statistically significant at $p \leq 0.05$.

Some changes were made to the data to facilitate correlation analyses. The $\text{Log}_{10} \text{TCID}_{50}/\text{ml}$ values listed as <2.00 were set to 1.0. Negative RT-PCR values were set to 1.0 and all RT-PCR values were normalized by transformation to log base 10 before analysis. Control group results were not included in the correlation analyses. Results for each pig were converted to an approximate area under the curve using trapezoidal rule. Area under the curve was computed for the entire study period, from the first observation to day 15, and from day 15 to the last observation, although only the entire study period is shown in the figures.

Results

Virus Isolation and $\text{Log}_{10} \text{TCID}_{50}/\text{ml}$ Quantification

Before exposure on the day of infection no animals tested positive for PRRSV. At 1 day after intranasal infection, only 13 animals in 5 groups tested positive for virus. However, at 3 days after infection all animals that were infected with field isolates, except for isolate 17198-6, were virus positive with mean $\log_{10} \text{TCID}_{50}/\text{ml}$ values ranging from 2.1 (SDSU-73) to 3.9 (MN 184). By contrast, animals inoculated with attenuated isolates were uniformly negative by cell culture. These results are provided in FIG. 1. Peak levels of viremia, from 3.6 to 4.6 $\log_{10} \text{TCID}_{50}/\text{ml}$ were attained on day 7 for four of five virulent isolates and titers remained near or above 2 $\text{Log}_{10} \text{TCID}_{50}/\text{ml}$ in all virulent virus groups for 21 days except for JA 142-infected pigs which had titers below that level.

The levels of viremia in the pigs inoculated with attenuated PRRSV isolates were lower than in pigs inoculated with virulent field isolates. The Abst-1 isolate, with the exception of day 3 post inoculation, was never re-isolated. Ingelvac® PRRS MLV viremia fluctuated between 0.5 and 1.0 $\text{Log}_{10} \text{TCID}_{50}/\text{ml}$ from days 7 to 28, and Ingelvac® PRRS ATP varied between 0.4 and 1.2 $\text{Log}_{10} \text{TCID}_{50}/\text{ml}$ from days 7 to 28. Attenuated isolate viruses were not recovered from serum after day 28, and virus was recovered from only two of the virulent field isolate groups, the pool-infected and MN 184-infected pigs through day 35 (also shown in FIG. 1). Nearly all pigs were nonviremic by virus isolation at days 42 and 49.

Overall, the more virulent isolates were observed to replicate faster and to higher titers in pigs than were the attenuated isolates. Pigs infected with the MN 184 isolate, in particular, showed a very rapid increase in virus replication beginning before day 3 and reaching a peak of over 4.5 $\text{Log}_{10} \text{TCID}_{50}/\text{ml}$ on day 7. After peaking, the MN 184 viremia steadily decreased but still maintained a significantly higher titer (t-test, $p \leq 0.05$) than all other isolates on days 28 and 35. A similar trend was observed in all of the remaining virulent groups, namely VR2332, JA 142, SDSU 73, and the pool (see, FIG. 1). Pigs infected with 17198-6 followed the same general trend described for the MN 184 infected group but not as closely.

Groups of pigs administered the attenuated isolates (Ingelvac® PRRS MLV, Ingelvac® PRRS ATP, and Abst-1) followed a different trend. They showed a moderate increase in viral titer beginning after day 3 that reached a peak between days 7 and 15 at a viral titer more than a log less than any of the virulent exposure groups and several orders of magnitude less than the MN 184-infected group. The titers observed in these attenuated exposure groups then declined to zero on or before day 35 (See FIG. 1).

Virus Quantification by Real Time RT-PCR

Figure 2:
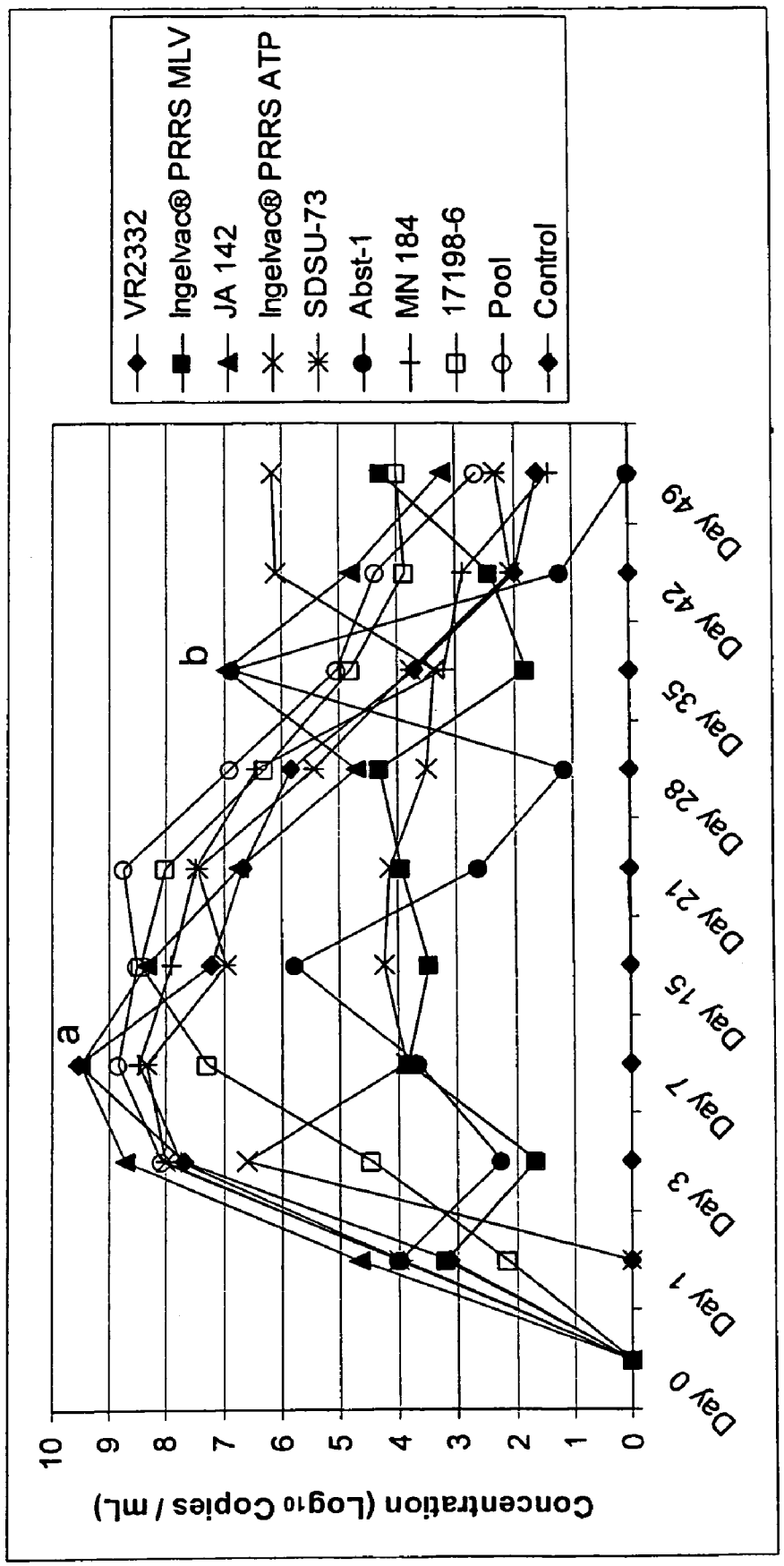
FIG. 2 is a graph of mean PRRSV virus concentration in serum in the swine test of Example 1, as measured by real time RT-PCR.

Levels of viremia were also determined by real time RT-PCR since it was possible that growth on CL2621 cells was not the same for all strains and because RT-PCR might be a more sensitive measure than growth on cells for viremia. As shown in FIG. 2, virulent exposure groups showed a dramatic increase in average concentration on day 1 and all groups peaked above 8 logs/ml between days 7 and 15. The virulent exposure group concentrations then gradually tapered off through the next several weeks, reaching concentrations below 4 logs/ml by day 49.

The attenuated strain exposure groups showed a much less dramatic increase in concentration that also began around day 1 and the average group titer never reached or exceeded 7 logs/ml (FIG. 2). The concentrations observed for the attenuated exposure groups were maintained at fluctuating levels showing a wide range in values in the weeks following the exposure. The fluctuations were primarily due to sporadically high values in a single pig. The three attenuated strain exposure groups all peaked on different days of the study. The Ingelvac® PRRS MLV group peaked at a concentration of 4.31 logs/ml on day 28, the Ingelvac® PRRS ATP group peaked at 6.58 logs/ml on day 3, and the Abst-1 group peaked at 6.85 logs/ml on day 35, which was the highest titer achieved by an attenuated isolate (FIG. 2). Additionally, the average concentration of the virulent isolate groups were observed to be significantly higher (P<0.05) than the average concentration of the attenuated strain groups on days 3 and 15, but on day 49 the average concentration of the virulent isolate groups was significantly lower (P<0.05) than that of the attenuated isolate groups.

HerdChek® PRRS ELISA 2XR

Figure 3:
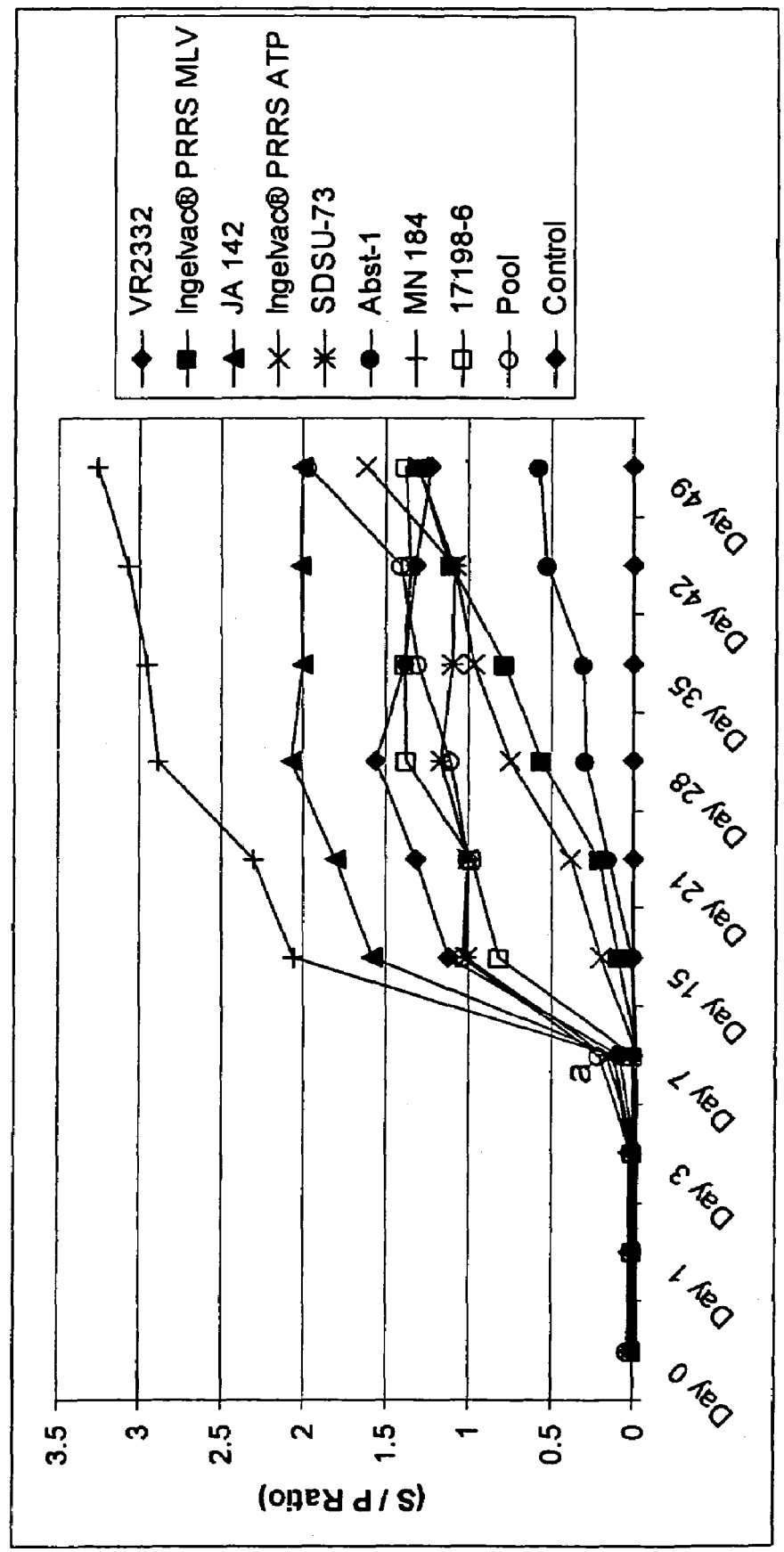
FIG. 3 is a graph of mean S/P ratios versus time using a commercial ELISA assay.

As shown by FIG. 3, the humoral immune response to PRRSV, as measured by HerdChek® PRRS ELISA 2XR S/P ratios, showed that the virulent isolate exposure group averages rose above the 0.4 cutoff for a positive result on day 15. By contrast, the attenuated strain exposure group averages were negative and all three groups remained below 0.4 until after day 21. The Ingelvac® PRRS MLV and Ingelvac® PRRS ATP groups showed positive results on day 28, but the Abst-1 group did not show an average S/P ratio over 0.4 until day 42.

Figure 4:
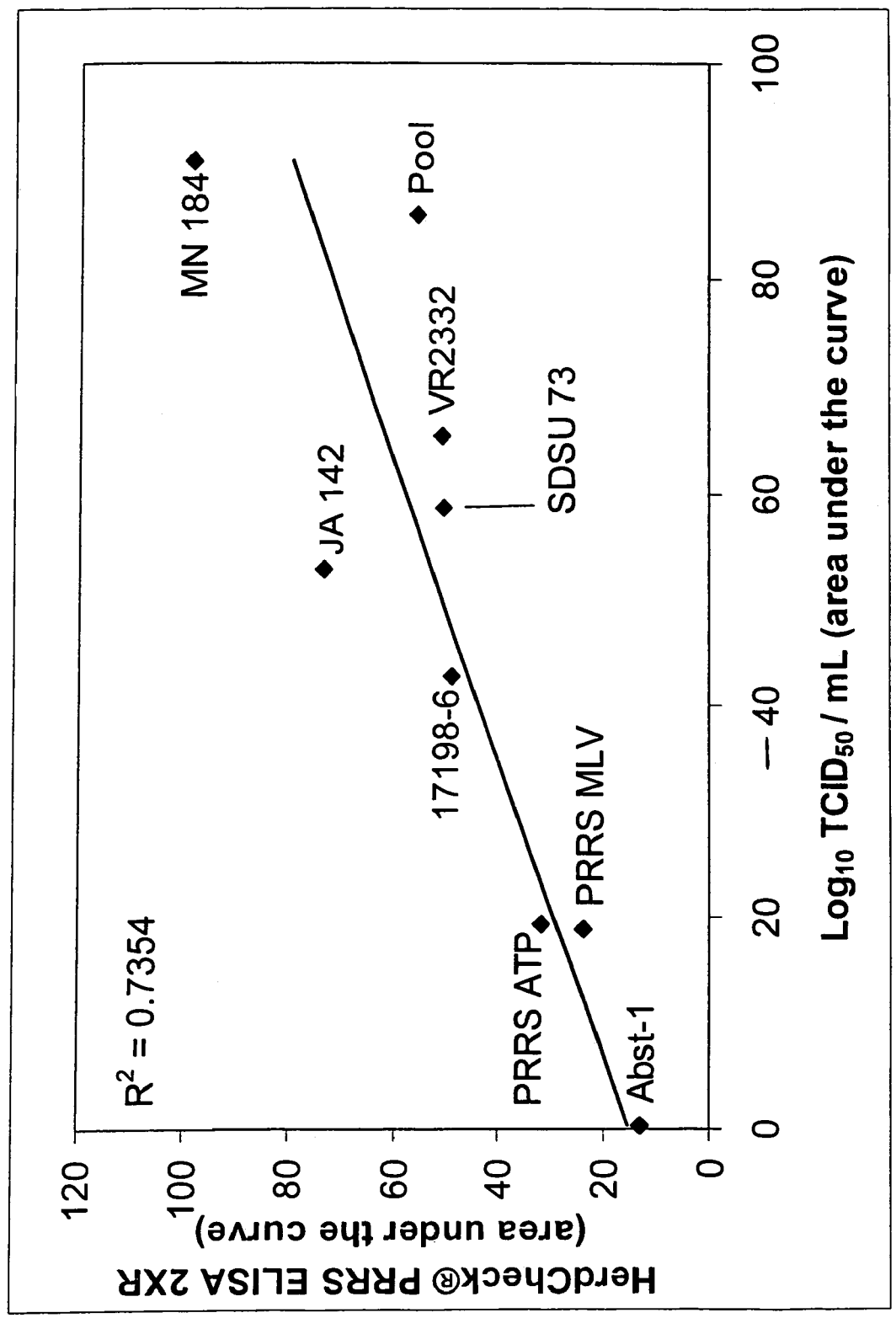
FIG. 4 is a graph illustrating repeated measures analysis for the commercial ELISA assay and the $Log_{10}$ $TCID_{50}$/ml data of Example 1, wherein the group average under the ELISA S/P ratio curve was plotted against the group average area under the $Log_{10}$ $TCID_{50}$/ml.
Figure 5:
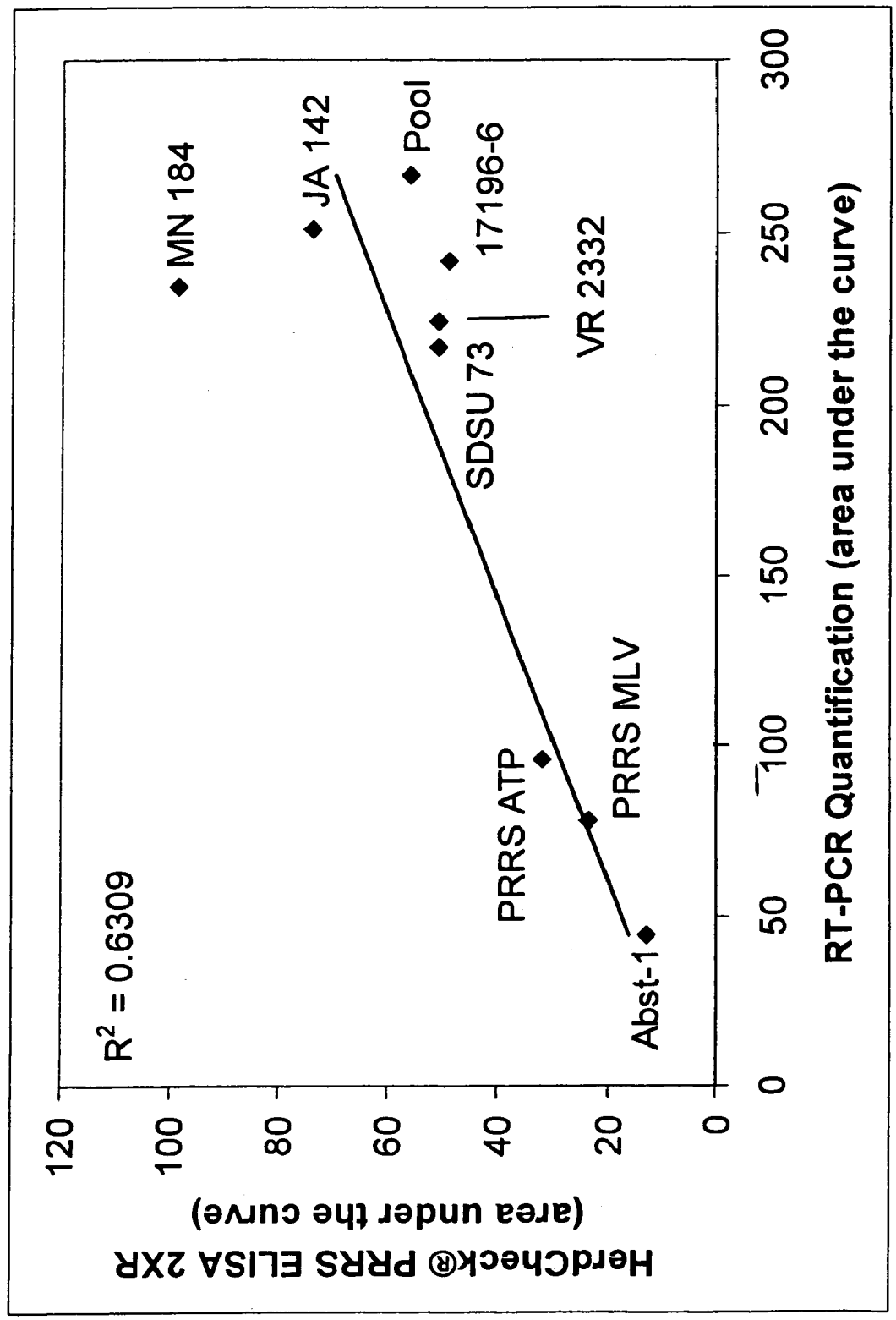
FIG. 5 is a graph illustrating repeated measures analysis for the commercial ELISA assay and RT-PCR concentration data of Example 1, wherein the group average area under the ELISA ratio curve was plotted against the group average area under the RT-PCR concentration curve.

In comparing the humoral response of groups infected with virulent isolates or the pool to groups inoculated with attenuated strains, it was clear that the kinetics and magnitude of the antibody response was associated with the level of viremia, particularly between 14 and 35 days after infection. This observation is further supported by the correlation between viremia levels and humoral antibody responses determined by paired comparisons of HerdChek® PRRS ELISA 2XR S/P ratios to either virus titration or RT-PCR. FIGS. 4 and 5 show that the humoral antibody response is closely associated with viral load over the entire study period with a correlation coefficient r=0.858 for virus titration and r=0.794 for RT-PCR. These associations were highly significant (p<0.0001 in each case). Moreover, attenuated strains show low antibody responses and viral loads, whereas virulent strains show high responses.

PRRSV Protein-Specific ELISA

Figure 6A:
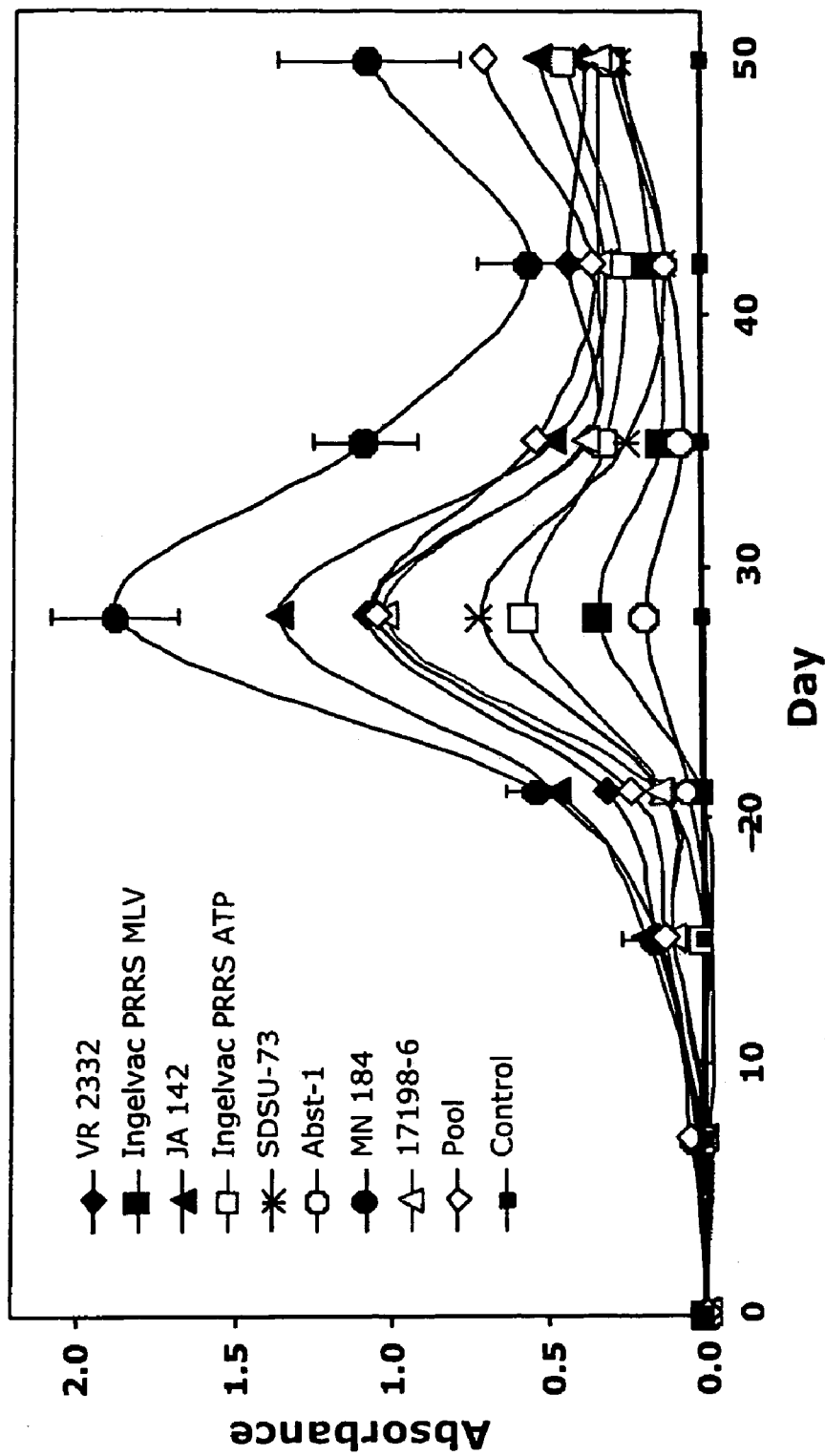
FIG. 6a is a graph of absorbance versus time for Example 1.
Figure 6:
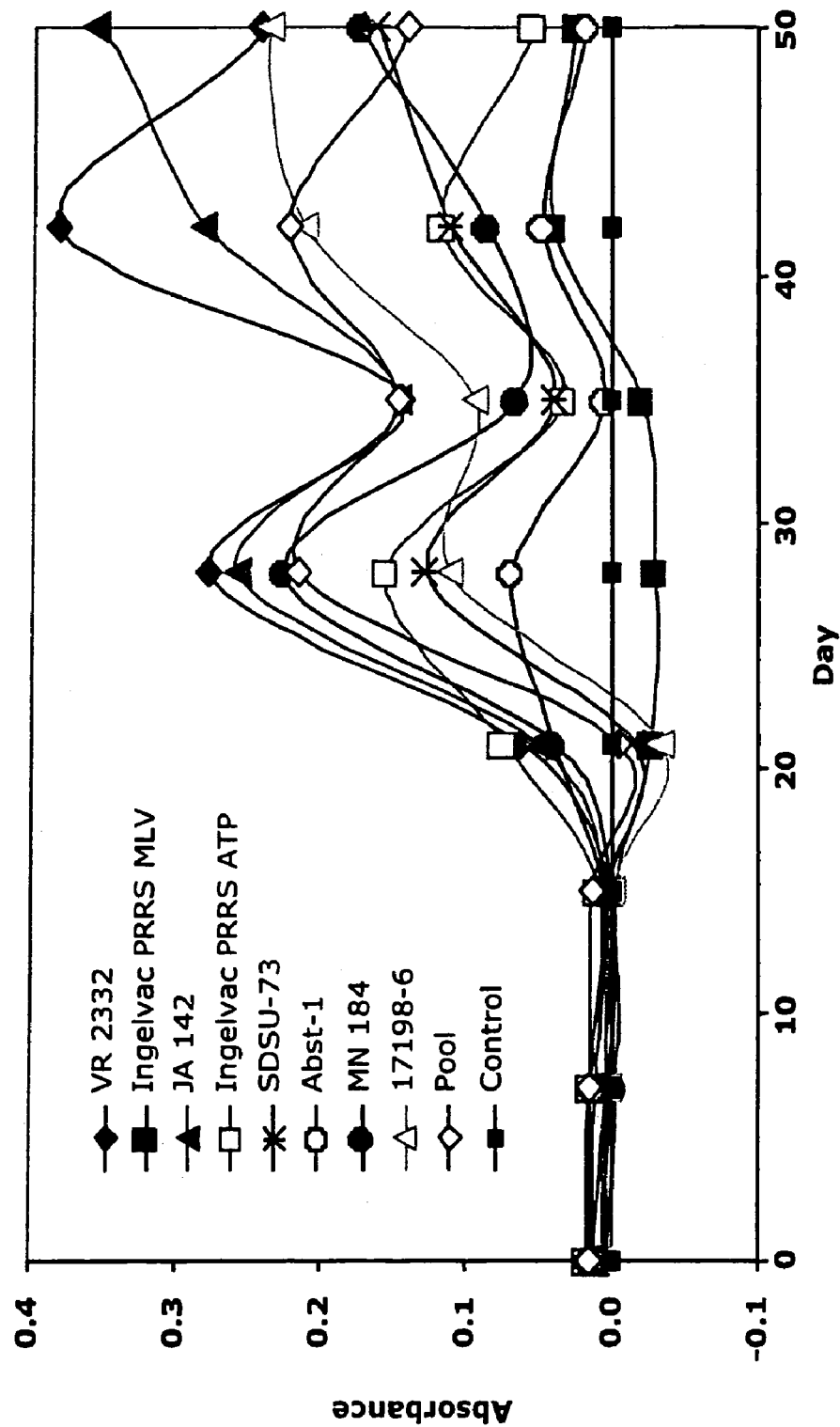
FIG. 6b is a graph of absorbance versus time, illustrating the effect of PRRSV isolate or strain on nsp-4 IgG response, wherein the data are the mean values of 10 animals, except where animals died.

To gain additional insight into the relationship between differences in PRRSV inocula and humoral immune responses, the antibody titers against N, the major structural protein, and nsp 4, an essential but minor nonstructural protease, were determined. FIG. 6a illustrates that the kinetics of the nucleocapsid anti-N IgG response were nearly identical in all groups of pigs, with a peak titer on day 28 followed by a sharp decline in the next 7-14 days, after which the levels were maintained or rose slightly between days 42 and 49.

The magnitude of the response for each strain was similar to that found in the HerdChek® PRRS ELISA 2XR results, and consistent with the levels of viremia. The lowest peak titers at day 28 were observed in the groups inoculated with attenuated strains, and the highest titer was attained in pigs infected with the highly virulent MN 184 isolate. By day 49 the anti-N titer was equivalent in all groups except for MN 184 and the pool, suggesting that the humoral response to MN 184 may be qualitatively different. Additionally, only 5 pigs survived to day 49 in each of these two groups, which is reflected in the increased standard error at day 49 in the MN 184 group.

Figure 7:
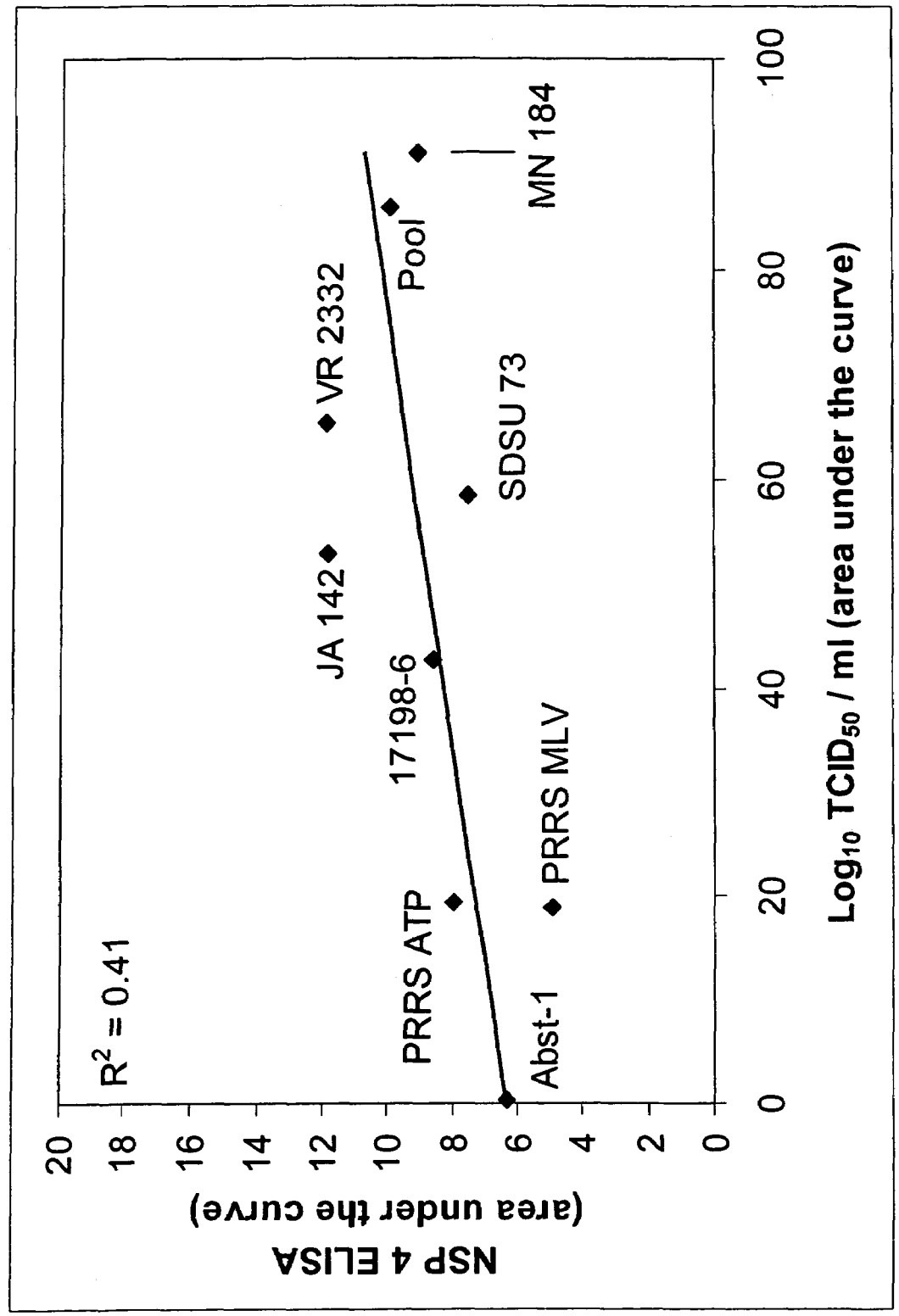
FIG. 7 is a graph illustrating repeated measures analysis using the nsp-4 and $log_{10}$ $TCID_{50}$/ml data of Example 1, wherein the group average area under the nsp-4 curve was plotted against the group average area under the $Log_{10}$ $TCID_{50}$/ml curve.

As shown by FIG. 6b, the IgG response to nsp 4 was substantially different than to N. No anti-nsp 4 antibody was detected before day 21, the overall response was much weaker, and no significant response was detected in the groups receiving Ingelvac® PRRS MLV and Abst-1. Moreover, the magnitude of the anti-nsp 4 response was not associated with level of viremia. The responses to VR 2332, JA 142, MN 184, and the pool were all equivalent, with a peak at day 28, followed by a decline at day 35, then rising again at day 42, whereas the magnitude, time course and duration of viremia varied among these four groups. FIG. 7 illustrates that when examining the repeated measures analysis, data for the nsp 4 ELISA compared to the $\text{Log}_{10}\ \text{TCID}_{50}$/ml data, it can be seen that there is no correlation between level of viremia and nsp 4 humoral antibody response.

Body Weight

There was no significant difference in the mean weight of any of the groups on day 0 of the experiment (P=0.099). On day 49 pigs inoculated with the attenuated strain Abst-1 had the highest mean weight, which was significantly higher then all other groups except for the control group (Table 3). Also, on day 49, the mean weights of all the virulent isolate exposure groups except for the 17198-6 group were significantly lower than the control group (Table 3). The mean weights of the attenuated strain exposure groups Ingelvac® PRRS MLV and Ingelvac® PRRS ATP and the control group were statistically equivalent (Table 3).

TABLE 3

Average Body Weights.

| Isolate | Day 0 | Day 49 |
|---|---|---|
| VR 2332 | 6.38[1] | 33.5[b] |
| Ingelvac ® PRRS MLV | 6.56 | 34.6* |
| JA 142 | 6.42 | 32.7[b] |
| Ingelvac ® PRRS ATP | 6.24 | 35.0* |
| SDSU-73 | 6.59 | 32.9[b] |
| Abst-1 | 6.69 | 39.4[a] |
| MN 184 | 6.73 | 23.7[c] |
| 17198-6 | 6.36 | 34.5* |
| Pool** | 6.51 | 23.0[c] |
| Control | 6.48 | 38.4* |

[1]Weights are in kg. There were no significant differences in mean wt at day 0.
*Indicates statistically equivalent weights among these groups on day 49.
**Pool was a mixture containing all eight isolates.
[a]Significantly greater than all groups except the Control group (p ≦ 0.05).
[b]Significantly less than the Control group.
[c]Significantly less than all other groups.

Clinical Scores

Increases in average clinical scores were observed in only four of the virulent exposure groups: JA 142, SDSU 73, MN 184, and Pool. These higher scores were maintained throughout the study while the remaining groups, both virulent and attenuated exposures, had essentially normal clinical scores for the duration of the study. The only major cause of changes in the average clinical scores observed in this study occurred when one or more animals died in the associated treatment group (Table 4).

TABLE 4

Mortality of Pigs after Exposure

| Group | Strain | Mortality | Day(s) of Death(s) |
|---|---|---|---|
| 1 | VR 2332 | 0/10 | N/A |
| 2 | Ingelvac ® PRRS MLV | 0/10 | N/A |
| 3 | JA 142 | 1/10 = 10% | 17 |
| 4 | Ingelvac ® PRRS ATP | 0/10 | N/A |
| 5 | SDSU 73 | 2/10 = 20% | 9, 23 |
| 6 | Abst-1 | 0/10 | N/A |
| 7 | MN 184 | 5/10 = 50% | 14, 14, 17, 23, 41 |
| 8 | 17198-6 | 0/10 | N/A |
| 9 | Pool** | 5/10 = 50% | 12, 16, 17, 21, 21 |
| 10 | Controls | 2/10* | 41, 48 |
|  | Attenuated PRRSV | 0/30 = 0% |  |
|  | Virulent PRRSV | 13/60 = 22% |  |

All deaths in treatment groups were attributed to moderate or severe non-suppurative interstitial pneumonia due to PRRSV with secondary bacterial infection.
*Deaths attributed to bacterial pneumonia with no PRRS involvement.
**Pool was a mixture containing all eight isolates.

Figure 8:
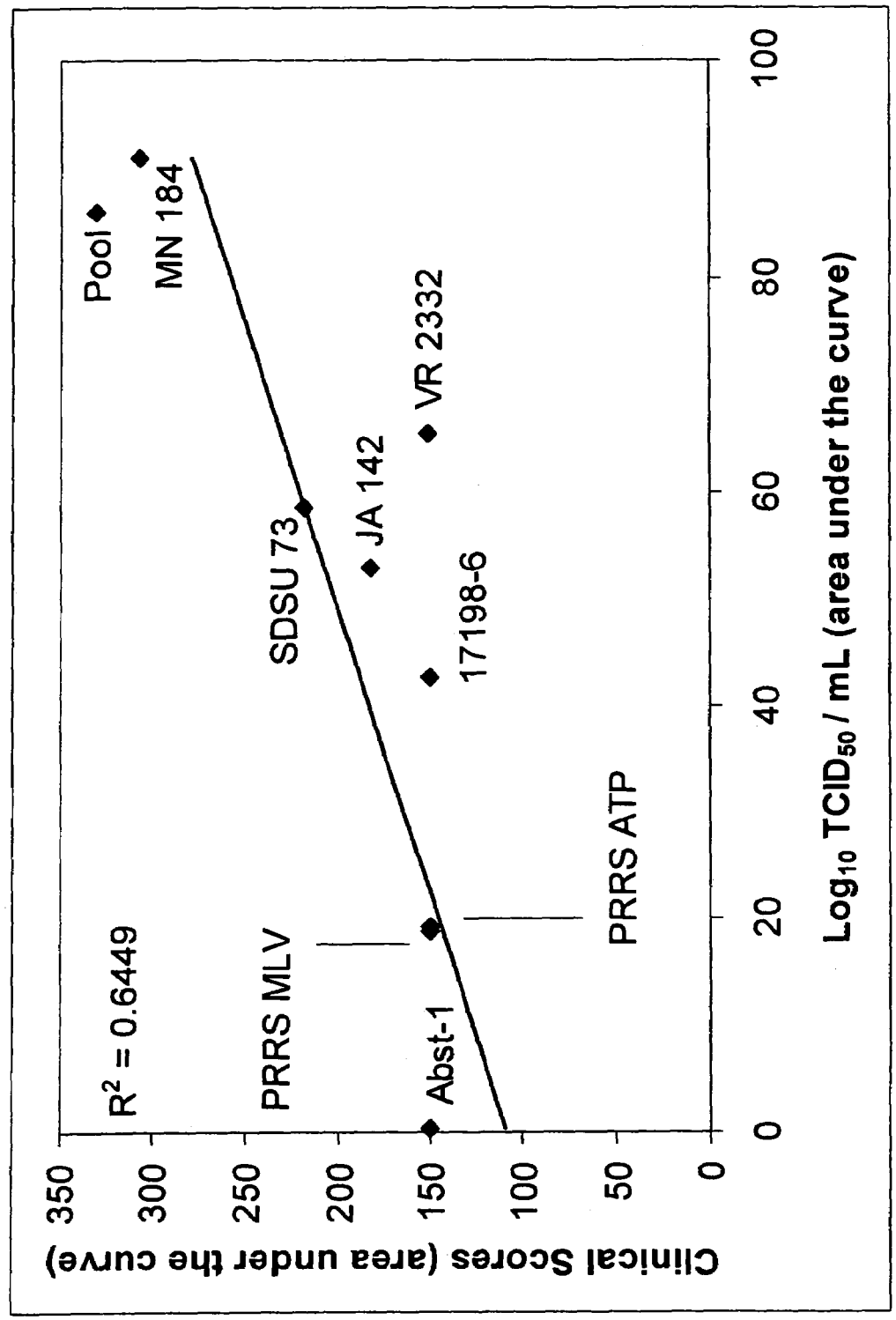
FIG. 8 is a graph of repeated measures analysis using the clinical scores and $log_{10}$ $TCID_{50}$/ml data of Example 1, wherein the group average under the clinical scores curve was plotted against the group average area under the $Log_{10}$ $TCID_{50}$/ml curve.

The severity of clinical disease was highly associated with viral load (p<0.001 for virus titration). As shown in FIG. 8, the clinical scores were highest for the groups infected with MN 184 and the Pool. Fifty percent of the pigs in each group died, and virus titration indicated that the level of infection was substantially higher than for all other groups. The differences in viral load as determined by RT-PCR were less marked (data not shown) and the correlation of clinical signs with viral load by RT-PCR was less than with virus titration (r=0.556 versus r=0.803, respectively). The clinical scores in group 10 (Control) increased after the death of two pigs from bacterial pneumonia. Both pigs were shown to be PRRSV negative by immunohistochemical staining of lung tissue, negative virus isolation and real-time PCR analyses, and the complete lack of seroconversion by HerdChek® PRRS ELISA 2XR or protein-specific ELISA. Later findings indicated that various bacterial pathogens were present in animals that died unexpectedly during the study these deaths were likely attributed to secondary bacterial infection (Table 5).

TABLE 5

Cause of Mortality after Exposure

| Pig # | Group | Cause of Death | Day of Death |
|---|---|---|---|
| 993 | JA 142 | PRRS & *Streptococcus suis* | 17 |
| 948 | Neg Control | *Arcanobacterium pyogenes* & *Pasteurella multocida* | 41 |
| 983 | Neg Control | *A. pyogenes* & *P. multocida* | 48 |
| 922 | SDSU 73 | PRRS and bacterial pneumonia* | 9 |
| 918 | SDSU 73 | PRRS and *Escherichia coli* | 23 |
| 973 | MN 184 | PRRS and *Actinobacillus suis* | 14 |
| 992 | MN 184 | PRRS and *A. suis* | 14 |
| 980 | MN 184 | PRRS and *E. coli* | 17 |
| 971 | MN 184 | PRRS and *E. coli* | 23 |
| 958 | MN 184 | PRRS and *E. coli* | 41 |
| 976 | Pool | PRRS and *A. suis* | 12 |
| 970 | Pool | PRRS and V *S. suis* | 16 |
| 972 | Pool | PRRS and *S. suis* | 17 |
| 995 | Pool | PRRS and *S. suis* | 21 |
| 969 | Pool | PRRS and *A. pyogenes* | 21 |

*The diagnostic report indicated "bacterial pneumonia" with no specific agent listed.

Discussion

One objective of this example was to examine various PRRSV isolates with known levels of virulence to determine if there was a relationship with in vivo replication that could be used to predict the virulence of PRRSV isolates without the necessity of performing controlled challenge experiments. Additionally, it was of interest to determine the relationship between isolate virulence, levels of viremia, and the humoral antibody response. Finally, it may be of interest to develop vaccines against the PRRSV isolates that are found to be virulent using the methods of the present invention. It would be a goal to have such vaccines provide some degree of protection against other virulent isolates; however, such cross-effectiveness may not be universal for all PRRSV isolates and further testing would be required. However, it is clear that the present invention provides an effective tool for identifying prime candidates for vaccine development.

In order to test PRRSV isolates under the same conditions it was necessary to use dosages of licensed vaccines that were below the minimum immunizing dose established with the USDA and that were not representative of a commercial dose. Also, the intranasal route of administration of the MLV vaccines used in the study was not in accordance with the USDA label and was only used to mimic a more natural exposure. The typical commercial dose of the modified live PRRS vaccines (Ingelvac PRRS and Ingelvac PRRS ATP) is much higher than what was used in this experimental trial. These experimentally low doses of modified live PRRS vaccine do not represent the actual product dosage and form used in the field and readily explains the reported serological response. Using a commercial dose of vaccine, serological titers as measured via the IDEXX assay would be detectable by day 14. In this trial using titers of approximately 3 logs, this serological response was delayed and lower. This was to be expected, but was done to insure consistency of titer administration between groups and to facilitate the analysis and comparison between virulent and attenuated isolates. Although not specifically addressed in this Example, the effect of dose is likely much more significant for an attenuated or less virulent virus than it is for a virulent field virus that can quickly grow in and be recovered at over 4 logs/ml in pig serum within 3-7 days of exposure. The higher recommended intramuscular commercial dose gives HerdChek® PRRS ELISA 2XR S/P ratios above the 0.4 cutoff by 14 days post vaccination which is one-half the amount of time observed for the doses used in this study (Roof et al., 2003). The nominal dose used in this study, $2 \times 10^3$ TCID$_{50}$ per animal, caused 50% mortality in groups that received isolate MN 184, and anti-nucleocapsid responses in all groups. Higher doses were not tested since excessive mortality in groups challenged with highly virulent strains would have compromised the study objectives. In addition, previous studies had shown no difference in clinical signs and viremia in young pigs inoculated with PRRSV isolate VR2332 at doses of $10^{2.2}$, $10^{3.2}$ and $10^{4.2}$ TCID$_{50}$ per animal.

Both the Log$_{10}$ TCID$_{50}$/ml and real time RT-PCR results showed that the viremia levels vary significantly among groups following PRRSV exposure. This indicates that the growth rate of PRRSV in pigs is a phenotypic characteristic of the virus independent of possible variation in pig susceptibility to infection. In addition, attenuation of PRRSV by adaptation to growth on CL2621 cells reduced not only its ability to grow in pigs, but altered the kinetics of viral replication so that peak viremia occurred at later times. A similar observation was also made by Chang et al. (2002), who showed that even a limited period of cell culture passage of the moderately virulent PRRSV isolate VR 2332 reduced viral growth in pigs and delayed significantly the time to peak viremia. However, a delayed time to peak viremia is not diagnostic for in vitro cell culture passage or for attenuation, since the highly virulent isolate 17198-6 also showed a delayed time to peak viremia.

Overall, virulent isolates showed substantially higher viremia levels in serum than did attenuated strains at equivalent doses of inoculation. For example, the highest observed virus titer in any of the attenuated isolate exposure groups was 1.22 logs on day 15 in pigs given Ingelvac® PRRS ATP, whereas the lowest titer of any virulent group on day 15 was 2.40 logs in the SDSU 73 group. The peak of viremia at days 3-7 and the levels of virus detected (all >3.5 logs/ml) was highly consistent among virulent PRRSV isolates, though MN 184 was significantly greater in its magnitude and duration, with virus titers still present on days 28 and 35. This supports the concept that highly virulent PRRSV isolates replicate to a substantially higher titer in vivo than do attenuated or lowly virulent isolates, but they do not establish a direct quantitative relationship between level of virulence and level or rate of in vivo growth among wild-type PRRSV (Haynes et al. 1997).

The real time RT-PCR results were statistically very similar to the $Log_{10}$ $TCID_{50}$/ml results, indicating that both methods measure relative levels of infectious virus among groups. The Pearson correlation coefficient between the RT-PCR and $Log_{10}$ $TCID_{50}$/ml day 7 data was 0.89 and for the average real time RT-PCR and $Log_{10}$ $TCID_{50}$/ml results was 0.88. The concentration values determined by real time RT-PCR may have been several orders of magnitude higher than $Log_{10}$ $TCID_{50}$/ml values for several reasons, including differences between the frequency of viral particles containing the target amplicon and particles that are fully infectious on CL2621 cells, and the presence of neutralizing antibodies that could lower infectivity (Dianzani et al., 2002). However, neutralizing antibody is unlikely to account for the difference, because it was observed at all time points, including times before which an anti-PRRSV antibody response had been produced.

The copies/ml values determined by real-time PCR were higher than the infectious titer values measured in cell culture by $TCID_{50}$/ml. This is because a standard curve based on the copies of genome of the virus is routinely used for quantitative PCR which directly amplifies a genomic sequence of the virus rather than known infectious virions. Biologic assays such as cell culture do measure the presence of infectivity, however, they may not count all of the infectious particles present in a preparation. Factors that could affect the infectious titer such as cell culture conditions and in vivo antibodies, which may neutralize virus, have been observed in other studies, underestimating the amount of infectious virus measured in $TCID_{50}$/ml in sera. Alternatively, some non-infectious or replication-defective virus may be present which would be reflected by higher copy numbers.

In general, the ELISA observations support the concept that the magnitude of the humoral immune response is related to the level of viral replication during acute infection. The trend indicated in FIGS. 4 and 5 illustrates this relationship. A slower and less intense humoral immune response was triggered by the cell-culture attenuated virus isolates, whereas a faster and more intense humoral immune response was triggered by the virulent isolates. In addition these observations also demonstrate that at least two factors, isolate type and infectious dose, impact relative S/P ratio values in the HerdChek® PRRS ELISA 2XR. Although the ELISA results shown in FIG. 3 indicate a clear positive or negative average group response, it is important to note the variability among individual animals. Some pigs within attenuated virus groups were positive before day 21, and some pigs in the virulent groups remained negative up to day 21.

Analysis of specific antibody responses to N and nsp 4 show that immune responses to PRRSV vary in intensity independently of the inoculating isolate. Antibody responses to the N protein in animals that were inoculated with the highly virulent isolates MN 184 and JA 142 showed a trend similar to that of all the isolates but to a higher magnitude. Pigs inoculated with MN 184 and JA142 also had the highest viral titers, as shown in FIGS. 1 and 2. This indicates that the level of humoral immune response may be related to the viral load in acute infection as measured by viral titer. Interestingly, the time course of response was the same in all groups, even though the time to peak titer was delayed for highly virulent strain 17198-6 and the attenuated strains. The nsp 4 antibody response, by contrast, was low at all of the time points and for all of the isolates, both attenuated and virulent. The time course of anti-nsp 4 response was equivalent in all of the groups despite differences in the time to peak viral load among groups, as observed for the anti-N antibody response. All pigs had low anti-nsp 4 responses as shown in FIG. 7.

These observations indicate that some of the PRRSV proteins elicit a more robust response from the host immune system regardless of exposure isolate virulence. However, the observations also indicate that the magnitude of the immune response to the more immunogenic proteins is likely related to the virulence of the exposure isolate, or the ability of the isolate to replicate in vivo. It also is possible that differences in antibody response might be due simply to genetic differences among isolates that result in differences in antigenic reactivity such that antibodies directed against N and nsp 4 of other isolates do not react or react poorly to the recombinant proteins expressed from isolate VR2332 that were used to coat the ELISA plates. However, several lines of evidence suggest that the observed differences in antibody levels reflect immunologically relevant responses. Isolate MN 184 shows the greatest genetic difference from VR2332, as determined by ORF 5 comparisons, yet has the highest anti-N antibody response. Kapur et al. (1996) showed previously that relative differences among PRRSV isolates in one open reading frame are also present in other open reading frames. Additionally, individual proteins contain conserved and nonconserved regions (e.g. Kapur et al., 1996) and extensive immunogenic reactivity may be directed toward the conserved epitopes (Ostrowski et al., 2002). Nevertheless, ELISA results based on antibody reactions with purified PRRSV proteins may be affected by genetic and antigenic variation, and these effects must be considered. Refolding of recombinant proteins was performed, but no differences were observed between ELISA plates coated with nonrefolded or refolded proteins.

It was noted that at approximately 4 to 5 weeks after inoculation, a relatively large decrease in the antibody response to both the N and nsp 4 proteins occurred. A similar peak of 1 to 2 weeks followed by a decline of antibody reactivity was previously noted by Foss et al. (2002) for GP5, the major envelope glycoprotein. Taken together, these observations suggest that the response to individual viral proteins likely does not represent the full picture of the pig's immune response to PRRSV since the humoral immune response as measured by the HerdChek® PRRS ELISA 2XR does not show a similar transient peak of antibody reactivity.

Reduced growth and mortality were the key correlates of virulence and viral in vivo growth rate. The lower mean weight observed in the virulent isolate exposure groups most likely reflected a difference in the ability of a PRRSV isolate to replicate in vivo and induce a more severe illness in the pig. These observations are consistent with previously reported data that PRRSV infection may cause anorexia with a 25 to 40 percent reduction in daily weight gain (Thacker, 2003). The clinical scores of animals exposed to the virulent isolates showed rapid increases shortly after the inoculation, whereas there was virtually no change in the scores of the attenuated virus exposure animals. This increase in clinical signs was reflected in the observed death rates of 50%, 20%, and 10% in the virulent exposure groups receiving PRRS isolates MN 184, SDSU 73, and JA 142, respectively. In contrast, the attenuated exposure groups incurred no deaths. The relationship between rapid viral growth and viral pathogenesis under the same conditions of viral exposure were most evident in comparing the groups exposed to MN 184 and Abst-1. The inoculation titers were virtually the same, 4.10 logs/ml and 4.18 logs/ml, respectively, and yet, as indicated in FIG. 8, there were remarkable differences in the way the two isolates affected pigs. The Abst-1 isolate was nearly inert, it hardly replicated in vivo and caused no clinical signs. By contrast, the MN 184 isolate replicated to extremely high titers in vivo and caused severe clinical signs, resulting in the death of 50% of exposed animals. Also notable, the group of pigs exposed to the pool of all virus isolates showed about the same virological, clinical, and immunological responses as pigs exposed to MN 184. This finding indicates that the most rapidly replicating virus in a mixed infection is likely to outcompete other isolates so that the net result is essentially the same as an infection with the single isolate having the highest growth potential.

The notable in vivo differences between virulent and attenuated PRRSV isolates shed light on the relationship between the virulence of an isolate and its in vivo growth and replication. When administered at equivalent doses in pigs, the more virulent isolates show $Log_{10}$ $TCID_{50}$/ml titers and RT-PCR concentrations that are exponentially higher than the attenuated isolates. The virulent isolates induce a more rapid and intense humoral immune response. The virulent isolates negatively affect weight gain and induce higher death rates and more severe clinical signs as compared to the attenuated isolates.

In conclusion, the example and tests in the present application indicate that attenuated and virulent PRRSV isolates induce remarkably different clinical signs, as well as immune responses that differ in intensity. These differences are attributed to the ability of the virus to replicate in vivo, a phenotypic characteristic that can be measured quantitatively in serum samples and may be developed for predicting the virulence of PRRSV isolates.

REFERENCES

The teachings and content of each of the following references are incorporated by reference herein.

Albina, E., Piriou, L., Hutet, E., Cariolet, R., L'Hospitalier, R., 1998. Immune Responses in Pigs Infected with Porcine Reproductive and Respiratory Syndrome Virus (PRRSV). *Vet. Immunol. Immunopathol.* 61, 49-66.

Andreyev, V. G., Wesley, R. D., Mengeling, W. L., Vorwald, A. C., Lager, K. M., 1997. Genetic Variation and Phylogenetic Relationships of 22 Porcine Reproductive and Respiratory Syndrome Virus (PRRSV) Field Strains Based on Sequence Analysis of Open Reading Frame 5. *Arch. Virol.* 142, 993-1001.

Cavanagh, D., 1997. Nidovirales: a New Order Comprising Coronaviridae and Arteriviridae. *Arch. Virol.* 142, 629-633.

Chang, C. C., Yoon, K. J., Zimmerman, J. J., Harmon, K. M., Dixon, P. M., Dvorak C. M. T., Murtaugh, M. P., 2002. Evolution of Porcine Reproductive and Respiratory Syndrome Virus During Sequential Passages in Pigs. *J. Virology.* 76, 4750-4763.

Grebennikova, T. V., Clouser, D. F., Vorwald, A. C., Musienko, M. I., Mengeling, W. L., Lager, K. M., Wesley, R. D., Biketov, S. F., Zaberezhny, A. D., Aliper, T. I., Nepoklonov, E. A., 2004. Genomic Characterization of Virulent, Attenuated, and Revertant Passages of North American Porcine Reproductive and Respiratory Syndrome Virus Strain. *Virology.* 321, 383-390.

Dianzani F., G. Anelli, E. Riva, O. Turriziani, L. Antonelli, S. Tyring, D. Carrasco, H. Lee, D. Nguyen, J. Pan, J. Poast, M. Cloyd, S. Baron. 2002. Is Human Immunodeficiency Virus Rna Load Composed Of Neutralized Immune Complexes? *Journal of Infectious Diseases.* 185:1051-1054.

Foss, D. L., Zilliox, M. J., Meier, W., Zuckermann, F., Murtaugh, M. P. 2002. Danger Signals Increase the Immune Response to Porcine Reproductive and Respiratory Syndrome Virus. *Virus Res.* 15, 557-566.

Halbur, P. G., Pallares, F. J., Rathje, J. A., Evans, R., Hagemoser, W. A., Paul, P. S., Meng, X. J., 2002. Effects of Different Us Isolates of Porcine Reproductive and Respiratory Syndrome Virus (PRRSV) on Blood and Bone Marrow Parameters of Experimentally Infected Pigs. *Vet Rec.* 21, 344-348.

Halbur, P. G., Paul, P. S., Meng, X. J., Lum, M. A., Andrews, J. J., Rathje, J. A., 1996. Comparative Pathogenicity of Nine Us Porcine Reproductive and Respiratory Syndrome Virus (PRRSV) Isolates in a Five-week-old Cesarean-derived, Colostrums-deprived Pig Model. *J. Vet. Diagn. Invest.* 8, 11-20.

Haynes, J. S., Halbur, P. G., Sirinarumitr, T., Paul, P. S., Meng, X. J., Huffman, E. L., 1997. Temporal and Morphologic Characterization of the Distribution of Porcine Reproductive and Respiratory Syndrome Virus (PRRSV) by in Situ Hybridization in Pigs Infected with Isolates of PRRSV That Differ in Virulence. *Vet. Pathol.* 34, 39-43.

Hill, H., 1990. Overview And History Of Mystery Swine Disease (Swine Infertility And Respiratory Syndrome). *In Mystery Swine Disease Communication Meeting. Denver, Colo.*, pp. 29-31.

Kapur, V., Elam, M. R., Pawlovich, T. M. Murtaugh, M. P. 1996. Genetic Variation In PRRS Virus Isolates In The Midwestern United States. *J. Gen. Virol.* 77, 1271-1276.

Key, K. F., Haqshenas, G., Guenette, D. K., Swenson, S. L., Toth, T. E., Meng, X. J., 2001. Genetic Variation And Phylogenetic Analyses Of The Orf5 Gene Of Acute Porcine Reproductive And Respiratory Syndrome Virus Isolates. Vet. Micro. 83, 249-263.

Labarque, G., Van Gucht, S., Van Reeth, K., Nauwynck, H., Pensaert, M., 2003. Respiratory Tract Protection Upon Challenge Of Pigs Vaccinated With Attenuated Porcine Reproductive And Respiratory Syndrome Virus Vaccines. *Vet. Micro.* 95, 187-197.

Meng, X. J., 2000. Heterogeneity of Porcine Reproductive and Respiratory Syndrome Virus: Implications for Current Vaccine Efficacy and Future Vaccine Development. *Vet. Micro.* 74, 309-329.

Mengeling, W. L., Lager, K. M., Vorwald, A. C., Clouser, D. F., 2003a. Comparative Safety and Efficacy of Attenuated Single-strain and Multi-strain Vaccines for Porcine Reproductive and Respiratory Syndrome. *Vet. Micro.* 93, 25-38.

Mengeling, W. L., Lager, K. M., Vorwald, A. C., Koehler, K. J., 2003b. Strain Specificity of the Immune Response of Pigs Following Vaccination with Various Strains of Porcine Reproductive and Respiratory Syndrome Virus. *Vet. Micro.* 93, 13-24

Mengeling, W. L., Lager, K. M., Vorwald, A. C., 1998. Clinical Effects of Porcine Reproductive and Respiratory Syndrome Virus on Pigs During the Early Postnatal Interval. *Amer. J Vet Res.* 59, 52-55.

Murtaugh, M. P., K. S. Faaberg, J. Laber, M. Elam, and V. Kapur. 1998. Genetic Variation In The PRRS Virus. *Adv. Exp. Med. Biol.* 440, 787-794.

Murtaugh, M. P., Xiao, Z., Zuckermann, F., 2002. Immunological Responses Of Swine To Porcine Reproductive And Respiratory Syndrome Virus Infection. *Viral Immunology.* 15, 533-547.

Nodelijk, G., de Jong, M. C. M., van Leengoed, L. A. M. G., Wensvoort, G., Pol, J. M. A., Steverink, P. J. G. M., Verheijden, J. H. M., 2001. A Quantitative Assessment Of The Effectiveness Of PRRSV Vaccination In Pigs Under Experimental Conditions. *Vaccine* 19, 3636-3644.

Ostrowski, M, Galeota, J. A., Jar, A. M., Platt, K. B., Osorio, F. A., Lopez, O. J. 2002. Identification Of Neutralizing And Normeutralizing Epitopes In The Porcine Reproductive And Respiratory Syndrome Virus Gp5 Ectodomain. *J. Virol.* 76, 4241-4250.

Opriessnig, T., Halbur, P. G., Yoon, K. J., Pogranichniy, R. M., Harmon, K. M., Evans, R., Key, K. F., Pallares, F. J., Thomas, P., Meng, X. J., 2002. Comparison Of Molecular And Biological Characteristics Of A Modified Live Porcine Reproductive And Respiratory Syndrome Virus (PRRSV) Vaccine (Ingelvac PRRS M1v), The Parent Strain Of The Vaccine (Atcc Vr2332), Atcc Vr2385, And Two Recent Field Isolates Of PRRSV. *J. Virol.* 76, 11837-11844.

Pejsak, Z., Stadejek, T., Markowska-Daniel, I., 1997. Clinical Signs And Economic Losses Caused By Porcine Reproductive And Respiratory Syndrome Virus In A Large Breeding Farm. *Vet. Micro.* 55, 317-322.

Reed, L., Muench, H., 1938. A Simple Method For Estimating Fifty Percent Endpoints. *Am J Hyg.* 27, 493-497.

Roof, M. B., Vaughn, E. M., Burkhart, K. M., Faaberg, K. S. 2003. Efficacy Of Modified Live Virus Porcine Reproductive And Respiratory Syndrome Virus Vaccines Against Heterologous Respiratory Challenge. *Proc. 4$^{th}$ Inter. Symp. Emerging Re-emerging Pig Diseases. pp.* 117-118.

Thacker, B., 2003. Clinical Manifestations Of PRRS Virus. In: Zimmerman, J, Yoon, K J (Eds.), 2003 *PRRS Compendium Second Edition. National Pork Board, Des Moines Iowa USA*, pp. 7-12.

Thanawongnuwech, R., Halbur, P. G., Ackermann, M. R., Thacker, E. L., Royer, R. L., 1998. Effects Of Low (Modified-live Virus Vaccine) And High (Vr-2385)-virulence Strains Of Porcine Reproductive And Respiratory Syndrome Virus On Pulmonary Clearance Of Copper Particles In Pigs. *Vet. Pathol.* 35, 398-406.

Yuan, S., Mickelson, D., Murtaugh, M. P., Faaberg, K. S., 2001. Erratum To "Complete Genome Comparison Of Porcine Reproductive And Respiratory Syndrome Virus Parental And Attenuated Strains". *Virus Research.* 79, 189-200.

We claim:

1. A method of predicting the virulence of a PRRS virus strain of unknown virulence, comprising the steps of administering a quantity of said PRRS virus strain into PRRS-free swine, allowing the virus to replicate in said swine for a period of from about 3-15 days, quantitatively measuring the rate of virus growth and/or the magnitude of viremia in said swine more than once during said period, and comparing said rate of growth or viremia magnitude with the rate of growth and/or viremia magnitude of more than one PRRS virus strain of known virulence as a predictor of virulence of a PRRS strain of unknown virulence.

2. The method of claim 1, said period being between from about 3 to 7 days.

3. The method of claim 1, including the step of measuring the magnitude of viremia during said period, and comparing such magnitude with the viremia magnitude of said known PRRS virus strain.

4. The method of claim 1, said PRRS virus being administered by a method selected from the group consisting of oral, intranasal, intramuscular, intra-lymph node, intradermal, intraperitoneal, subcutaneous, and combinations thereof.

5. The method of claim 1, said viremia being measured by $Log_{10}$ TCID50/ml, reverse transcriptase-polymerase chain reaction, PRRS specific ELISA, PRRS protein-specific ELISA, and combinations thereof.

6. The method of claim 1, further including the step of observing said swine for clinical signs of PRRS infection after administration of said PRRS strain.

7. The method of claim 6, said clinical signs including respiratory signs, behavior, coughing, and combinations thereof.

8. The method of claim 1, further including the step of predicting that the PRRS strain will be of high virulence when its rate of growth or viremia magnitude are similar to that of a strain with high virulence.

9. The method of claim 1, further including the step of predicting that the PRRS strain will be of low virulence when its rate of growth or viremia magnitude are similar to that of a strain of low virulence.

10. The method of claim 1, said administered amount of PRRS virus being up to about 5 ml of innocula having a viral concentration of up to 5.0 $Log_{10}$ $TCID_{50}$/ml.

11. A method of predicting the virulence of a PRRS virus strain of unknown virulence, comprising the steps of administering a quantity of said PRRS virus strain into PRRS-free swine, allowing the virus to replicate in said swine for a period of from about 3-15 days, quantitatively measuring the rate of virus growth and/or the magnitude of viremia using $Log_{10}$ $TCID_{50}$/ml in said swine more than once during said period, and comparing said rate of growth or viremia magnitude with the rate of growth and/or viremia magnitude of more than one PRRS virus strain of known virulence as a predictor of virulence of a PRRS strain of unknown virulence.

* * * * *

UNITED STATES PATENT AND TRADEMARK OFFICE
CERTIFICATE OF CORRECTION

| | | |
|---|---|---|
| PATENT NO. | : 7,632,636 B2 | Page 1 of 1 |
| APPLICATION NO. | : 11/022262 | |
| DATED | : December 15, 2009 | |
| INVENTOR(S) | : Michael Roof | |

It is certified that error appears in the above-identified patent and that said Letters Patent is hereby corrected as shown below:

On the title page,

[*] Notice:     Subject to any disclaimer, the term of this patent is extended or adjusted under 35 USC 154(b) by (662) days Delete the phrase "by 662 days" and insert -- by 738 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,632,636 B2 |
| APPLICATION NO. | : 11/022262 |
| DATED | : December 15, 2009 |
| INVENTOR(S) | : Roof et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this

Second Day of November, 2010

David J. Kappos
*Director of the United States Patent and Trademark Office*